US009951130B2

(12) United States Patent
Schmidt et al.

(10) Patent No.: US 9,951,130 B2
(45) Date of Patent: Apr. 24, 2018

(54) IL-6 ANTAGONISTS AND USES THEREOF

(71) Applicant: ELEVEN BIOTHERAPEUTICS, INC., Cambridge, MA (US)

(72) Inventors: Michael March Schmidt, Boston, MA (US); Thomas M. Barnes, Brookline, MA (US); David V. Erbe, Arlington, MA (US); Eric Steven Furfine, Concord, MA (US); Alison Tisdale, Belmont, MA (US)

(73) Assignee: ELEVEN BIOTHERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/508,068

(22) Filed: Oct. 7, 2014

(65) Prior Publication Data

US 2015/0125468 A1 May 7, 2015

Related U.S. Application Data

(63) Continuation-in-part of application No. PCT/US2013/069279, filed on Nov. 8, 2013.

(60) Provisional application No. 61/831,699, filed on Jun. 6, 2013, provisional application No. 61/723,972, filed on Nov. 8, 2012.

(51) Int. Cl.
*C07K 16/24* (2006.01)
*A61K 39/00* (2006.01)

(52) U.S. Cl.
CPC ...... *C07K 16/248* (2013.01); *A61K 2039/505* (2013.01); *C07K 2317/24* (2013.01); *C07K 2317/33* (2013.01); *C07K 2317/34* (2013.01); *C07K 2317/565* (2013.01); *C07K 2317/71* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,548,990 A | 10/1985 | Mueller et al. |
| 4,816,567 A | 3/1989 | Cabilly et al. |
| 5,223,409 A | 6/1993 | Ladner et al. |
| 5,225,539 A | 7/1993 | Winter |
| 5,476,996 A | 12/1995 | Wilson et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,762 A | 12/1997 | Queen et al. |
| 5,698,797 A | 12/1997 | Fontanille et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,165,745 A | 12/2000 | Ward et al. |
| 6,180,370 B1 | 1/2001 | Queen et al. |
| 6,277,375 B1 | 8/2001 | Ward |
| 7,820,155 B2 | 10/2010 | Way |
| 8,536,308 B2 | 9/2013 | Way et al. |
| 2003/0082630 A1 | 5/2003 | Kolkman et al. |
| 2003/0157561 A1 | 8/2003 | Kolkman et al. |
| 2004/0009222 A1 | 1/2004 | Chou et al. |
| 2009/0130114 A1 | 5/2009 | Qian et al. |
| 2009/0202526 A1 | 8/2009 | Pons |
| 2010/0034809 A1 | 2/2010 | Diefenbach-Streiber et al. |
| 2011/0045025 A1 | 2/2011 | Middaugh et al. |
| 2011/0171241 A1 | 7/2011 | Dix et al. |
| 2012/0005773 A1 | 1/2012 | Aasen et al. |
| 2014/0017244 A1 | 1/2014 | Duerr et al. |
| 2015/0125468 A1 | 5/2015 | Schmidt et al. |
| 2015/0239970 A1 | 8/2015 | Bee et al. |

FOREIGN PATENT DOCUMENTS

| | | |
|---|---|---|
| CN | 101346395 | 1/2009 |
| CN | 102224169 | 10/2011 |
| WO | 9117271 A1 | 11/1991 |
| WO | 9201047 A1 | 1/1992 |
| WO | 9203918 A1 | 3/1992 |
| WO | 9209690 A2 | 6/1992 |
| WO | 9215679 A1 | 9/1992 |
| WO | 9218619 A1 | 10/1992 |
| WO | 9220791 A1 | 11/1992 |
| WO | 9301288 A1 | 1/1993 |
| WO | 9306213 A1 | 4/1993 |
| WO | 9311161 A1 | 6/1993 |
| WO | 9312227 A1 | 6/1993 |
| WO | 9413804 A1 | 6/1994 |
| WO | 9425585 A1 | 11/1994 |

(Continued)

OTHER PUBLICATIONS

Vajdos et al. (J Mol Biol. Jul. 5, 2002;320(2):415-28 at 416).*
Brown et al. (J Immunol. May 1996;156(9):3285-91.*
Vajdos et al. (J Mol Biol. Jul. 5, 2002;320(2):415-28).*
Brown et al. (J Immunol. May 1996;156(9):3285-91).*
Agarwal et al., "Rodent Models of Experimental Autoimmune Uveitis" Methods in Mol Biol, 900:443-469 (2012).

(Continued)

*Primary Examiner* — Brian Gangle
*Assistant Examiner* — Andrea K McCollum
(74) *Attorney, Agent, or Firm* — McDonnell Boehnen Hulbert & Berghoff LLP

(57) ABSTRACT

Interleukin 6 (IL-6) antagonists are provided that are specific for binding to site II of IL-6. Methods of using such inhibitors to treat IL-6 related diseases, e.g., disease of the eye such as diabetic macular edema are disclosed.

20 Claims, 4 Drawing Sheets

(56) References Cited

FOREIGN PATENT DOCUMENTS

| WO | 9627011 A1 | 9/1996 |
|---|---|---|
| WO | 9703461 A1 | 1/1997 |
| WO | 9713852 A1 | 4/1997 |
| WO | 9823289 A1 | 6/1998 |
| WO | 9824884 A1 | 6/1998 |
| WO | 9850431 A2 | 11/1998 |
| WO | 9945962 A1 | 9/1999 |
| WO | 0034784 A1 | 6/2000 |
| WO | 0114424 A2 | 3/2001 |
| WO | 0243478 A2 | 6/2002 |
| WO | 2004045507 A2 | 6/2004 |
| WO | WO 2006/020114 A2 | 2/2006 |
| WO | 2006028936 A2 | 3/2006 |
| WO | 2007076927 A1 | 7/2007 |
| WO | WO2007104529 A2 | 9/2007 |
| WO | 2008144763 A2 | 11/2008 |
| WO | 2010/060768 | 6/2010 |
| WO | 2014074905 A1 | 5/2014 |

OTHER PUBLICATIONS

Altschul, et al "Basic Local Alignment Search Tool" J. Mol. Biol. (1990) 215:403-410.
Altschul, et al "Gapped Blast and PSI-Blast: a new generation of protein database search programs" Nucleic Acids Research (1997) 25(17):3389-3402.
Asquith et al., "Animal models of Rheumatiod Arthritis" Euro. J. Immunol (2009) 39:2040-2044.
Barbas, et al., "Assembly of combinatorial antibody libraries on phage surfaces: The gene III site." PNAS USA (1991) 88:7978-7982.
Boder et al., "Directed evolution of antibody fragments with monovalent femtomolar antigen-binding affinity" PNAS USA (2000) 97:10701-10705.
Caspi et al., "Understanding Autoimmune Uveitis through Animal Models." Investigative Opthamology Visual Science (2011) 52(3):1873-1879.
Chao et al., "Isolating and engineering human antibodies using yeast surface display" Nature Protocols (2006) 1:755-768.
Chothia et al, "Canonical Structures for the Hypervariable Regions of Immunoglobulins" J. Mol. Biol (1987) 196:901-917.
Chothia et al, "Conformations of immunoglobulin hypervariable regions" Nature (1989) 342:878-883.
Einmahl et al., "Therapeutic applications of viscous and injectable poly(ortho esters)" Advanced Drug Delivery Reviews (2001) 53:45-73.
Finch et al., "Whole-Molecule Antibody Engineering: Generation of a High-Affinity Anti-IL-6 Antibody with Extended Pharmacokinetics," Journal of Molecular Biology (2011) 411:791-807.
Funatsu, et al "Vitreous levels of interleukin-6 and vascular endothelial growth factor are related to diabetic macular edema" Ophthalmology (2003) 110(9):1690-1696.
Ghelardi et al., "A Mucoadhesive Polymer Extracted from Tamarind Seed Improves the Intraocular Penetration and Efficacy of Rufloxacin in Topical Treatment of Experimental Bacterial Keratitis" Antimicrobial Agents and Chermotherapy (2004) 48(9):3396-3401.
Gram et al., "In vitro selection and affinity maturation of antibodies from a naive combinatorial immunoglobulin library." PNAS USA (1992) 89:3576-3580.
Griffiths et al., "Human anti-self antibodies with high specificity from phage display libraries." The EMBO Journal (1993) 12(2):725-734.
Haruta et al., "Blockade of Interleukin-6 Signaling Suppresses Not Only Th17 but Also Interphotoreceptor Retinoid Binding Protein-Specific Th1 by Promoting Regulatory T Cells in Experimental Autoimmune Uveoretinitis." Invest. Opthal. Vis. Sci. (2011) 52(6):3264-3271.
Hawkins et al., "Selection of phage antibodies by binding affinity: Mimicking affinity maturation." Journal of Molecular Biology (1992) 226(3):889-896.
Hoogenboom et al. "Multi-subunit proteins on the surface of filamentour phage: methodologies for displaying antibody (Fab) heavy and light chains" Nucl. Acids. Res. (1991) 19(15):4133-4137.
Huse, et al., "Generation of a Large Combinatorial Library of the Immunoglobulin Repertoire in Phage Lambda." Science (1989) 246:1275-1281.
International Search Report for PCT/US2013/069279, date of mailing Mar. 7, 2014.
Izumi-Nagai et al., "Interleukin-6 Receptor-Mediated Activation of Signal Transducer and Activator of Transcription-3 (STAT3) Promotes Choroidal Neovascularization" American Journal of Pathology (2007) 170(6):2149-2158.
Kalai et al., "Analysis of the mechanism of action of anti-human interleukin-6 and anti-human interleukin-6 receptor-neutralising monoclonal antibodies" Eur. J. Biochem. (1997) 249:690-700.
Kauffman et al., "Cytokines in Vitreous Humor: Interleukin-6 is Elevated in Proliferative Vitreoretinopathy" Invest Opthalmol Vis Sci (1994) 35(3):900-906.
Kohler et al, "Continuous cultures of fused cells secreting antibody of predefined specificity" Nature, 256:495-497 (1975).
Krzystolik et al., "Prevention of Experimental Choroidal Neovascularization with Intravitreal Anti-Vascular Endothelial Growth Factor Antibody Fragment" Arch Ophthalmol (2002) 120:338-346.
Martin et al., "Crystal Structure at 2.8 A of an FcRn/Heterodimeric Fc Complex: Mechanism of pH-Dependent Binding" Molecular Cell (2001) 7:867-877.
Miao et al., "Inflammatory cytokines in aqueous humor of patients with choroidal neovascularization" Molecular Vision (2012) 18:574-580.
Noma et al., "Aqueous humour levels of cytokines are correlated to vitreous levels and severity of macular oedema in branch retinal vein occlusion" Eye (2008) 22:42-48.
Pearson, "Effective protein sequence comparison" Methods of Enzymology (1996) 266:227-268.
Pearson, "Empirical statistical estimates for sequence similarity searches" Journal of Molecular Biology (1998) 276 (1):71-84.
Pearson, W., "Rapid and Sensitive Sequence Comparison with FASTP and FASTA" Methods Enzymol (1990) 183:63-98.
Tomizuka et al., "Double trans-chromosomic mice: Maintenance of two individual human chromosome fragments containing Ig heavy and k loci and expression of fully human antibodies." PNAS USA (2000) 97:722-727.
Yoshimura et al., "Involvement of Th17 cells and the effect of anti-IL-6 therapy in autoimmune uveitis." Rheum. (2009) 48:347-354.
Yuuki et al, "Inflammatory cytokines in vitreous fluid and serum of patients with diabetic vitreoretinopathy" Journal of Diabetes and its Complications (2001) 15(5):257-259.
Rudikoff, S., et al., "Single amino acid substitution altering antigen-binding specificity", Proceedings of the National Academy of Sciences, 79:1979-1983 (1982).
Winkler, K., et al., "Changing the antigen binding specificity by single point mutations of an anti-p24 (HIV-1) antibody", The Journal of Immunology, 165:4505-4514 (2000).
Chien, N., et al., "Significant structural and functional change of an antigen-binding site by a distant amino acid substitution: Proposal of a structural mechanism", Proceedings of the National Academy of Sciences, 86:5532-5536 (1989).
Tenhumberg, et al., "Structure-guided Optimization of the Interleukin-6 Trans-signaling Antagonist," Journal of Biological Chemistry, 283:27200-27207 (2008).
Magdelaine-Beuzelin, et al., "Therapeutic antibodies in ophthalmology: Old is new again", mAbs, 2:176-180 (2010).

* cited by examiner

SEQUENCE LISTING

```
<160> NUMBER OF SEQ ID NOS: 30

<210> SEQ ID NO 1
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30
```

Leu Ile Glu Trp Val Arg Gln Ala Pro Gly Gln Gly Leu Glu Trp Met
          35                  40                  45

Gly Val Ile Thr Pro Ser Gly Thr Ile Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
              85                  90                  95

Ala Arg Ser Arg Trp Asp Pro Leu Tyr Tyr Ala Leu Glu Tyr Trp
             100                 105                 110

Gly Gln Gly Thr Thr Val Thr Val Ser Ser Ala Ser Thr Lys Gly Pro
             115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                 165                 170                 175

Ala Val Leu Gln Ser Ser Gly Leu Tyr Ser Leu Ser Ser Val Val Thr
                 180                 185                 190

Val Pro Ser Ser Leu Gly Thr Gln Thr Tyr Ile Cys Asn Val Asn
             195                 200                 205

His Lys Pro Ser Asn Thr Lys Val Asp Lys Lys Val Glu Pro Lys Ser
210                 215                 220

Cys
225

<210> SEQ ID NO 2
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
             20                  25                  30

Gly Ile Pro Phe Met Asn Trp Tyr Gln Gln Lys Pro Gly Gln Pro Pro
             35                  40                  45

Lys Leu Leu Ile Tyr Ala Ala Ser Asn Arg Gly Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Glu
              85                  90                  95

Glu Val Pro Leu Thr Phe Gly Gln Gly Thr Lys Leu Glu Ile Lys Arg
             100                 105                 110

Thr Val Ala Ala Pro Ser Val Phe Ile Phe Pro Pro Ser Asp Glu Gln
             115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 3
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Gly Tyr Ala Leu Ser Asn Tyr Leu Ile Glu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Ile Thr Pro Gly Ser Gly Thr Ile Asn
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Arg Trp Asp Pro Leu Tyr Tyr Tyr Ala Leu Glu Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ser Glu Ser Val Asp Asn Tyr Gly Ile Pro Phe Met Asn
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ala Ser Asn Arg Gly Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Ser Glu Glu Val Pro Leu Thr
1               5
```

```
<210> SEQ ID NO 10
<400> SEQUENCE: 10

000

<210> SEQ ID NO 11
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

```
Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 12
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 13
<211> LENGTH: 122
<212> TYPE: PRT
<213> ORGANISM: Mus sp.
```

```
<400> SEQUENCE: 13

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Ser Asn Tyr
            20                  25                  30

Leu Ile Glu Trp Val Lys Gln Arg Pro Gly Gln Gly Leu Glu Trp Ile
        35                  40                  45

Gly Val Ile Thr Pro Gly Ser Gly Thr Ile Asn Tyr Asn Glu Lys Phe
    50                  55                  60

Lys Gly Lys Ala Val Leu Thr Ala Asp Lys Ser Ser Ser Thr Val Tyr
65                  70                  75                  80

Met Gln Leu Ser Ser Leu Thr Ser Asp Asp Ser Ala Val Tyr Phe Cys
                85                  90                  95

Ala Lys Ser Arg Trp Asp Pro Leu Tyr Tyr Ala Leu Glu Tyr Trp
            100                 105                 110

Gly Gln Gly Thr Ser Val Thr Val Ser Ser
            115                 120

<210> SEQ ID NO 14
<211> LENGTH: 111
<212> TYPE: PRT
<213> ORGANISM: Mus sp.

<400> SEQUENCE: 14

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Leu Thr Phe Gly Ala Gly Thr Lys Leu Glu Leu Lys
            100                 105                 110

<210> SEQ ID NO 15
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser
        115                 120

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Met Thr Gln Ser Pro Asp Ser Leu Ala Val Ser Leu Gly
 1               5                  10                  15

Glu Arg Ala Thr Ile Asn Cys Arg Ala Ser Glu Ser Val Asp Asn Tyr
             20                  25                  30

Gly Ile Ser Phe Met Asn Trp Tyr Gln Gln Lys Pro Gly Gln Pro Pro
         35                  40                  45

Lys Leu Leu Ile Tyr Ala Ala Ser Asn Gln Gly Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Val Pro Leu Thr Phe Gly Gln Gly Thr Lys Leu Glu Ile Lys
            100                 105                 110

<210> SEQ ID NO 17
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Leu Ser Asn Tyr
             20                  25                  30

Leu Ile Glu Trp Val Arg Gln Ala Pro Gly Gln Gly Leu Glu Trp Met
         35                  40                  45

Gly Val Ile Thr Pro Gly Ser Gly Thr Ile Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser
        115                 120
```

```
<210> SEQ ID NO 18
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gly Gly Thr Lys Leu Glu Ile Lys Arg
            100                 105                 110

Thr Val

<210> SEQ ID NO 19
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

```
Val Pro Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 20
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caagtgcagc tggtgcagtc aggggccgag gttaagaagc agggagcag cgtcaaggta      60 tcttgtaaag cgtctggtta cgcccttca aactacctga tcgaatgggt gaggcaggct     120
cccggccaag gcctggaatg gatgggagtt atcaccctg ggagcggcac cattaattac     180
gcccagaaat tcagggacg agtgacgatt accgccgacg agtccaccag tactgcctac     240
atggagctgt cctcactccg cagcgaggac acggcagttt actactgcgc ccggagtcga     300
tgggaccctc tttactatta tgctctggaa tactggggcc agggaacgac cgttacagtg     360
tcatctgcta gcacaaaagg accatcagtc ttcccacttg ctccttcatc taagagcaca     420
agtggtggca ctgcagccct ggctgcctg gtgaaagatt atttccccga acctgttaca     480
gtttcttgga actccggtgc actgacatcc ggagtacaca ctttcccagc tgtgctgcag     540
```

```
agctcaggac tgtatagcct gtcttcggtg gtcactgttc catcgtcgag tcttggcaca    600
cagacatata tttgcaacgt caatcacaag ccctccaaca caaaagtgga taagaaggtc    660
gagcccaaat cttgtgacaa gacccatacg tgtcctccct gtcccgcccc tgaactgctg    720
ggaggccctt ctgtgttcct gttcccacct aagccaaagg acactctgat gatcagccgg    780
actcccgagg ttacctgtgt ggtggtggat gtgtctcatg aagaccctga ggttaagttc    840
aattggtacg tggatggcgt cgaggtgcat aacgcaaaaa ccaagccgag agaggagcag    900
tacaatagca cctatagagt agtgagcgtc ctgactgtct acatcagga ttggctcaat     960 ggtaaagaat ataagtgcaa ggtaagcaac aaggccctac ccgcaccaat agagaagacc   1020
atctccaagg cgaaaggtca gcccagggag ccccaggttt atacactgcc tcccctcacgc  1080 gacgaattaa caaagaatca ggtgtctctc acctgtctcg tcaagggctt ttacccttcc   1140
gacatcgccg tggagtggga atccaatggc cagcctgaga acaattataa gacaactccc   1200
ccagtcctgg attcagatgg gtcgttcttt ctatatagta agttgaccgt ggataagtct   1260
cgctggcaac aggggaacgt gttctcttgc tctgttatgc atgaagcgct gcacaatcat   1320
tatacccaga agtccctgtc cctgagcccc gggaag                            1356
```

<210> SEQ ID NO 21
<211> LENGTH: 212
<212> TYPE: PRT
<213> ORGANISM: Homo sapiens

<400> SEQUENCE: 21

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
        50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

```
<210> SEQ ID NO 22
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 23
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

Met Glu Leu Ser Ser Leu Arg Ser Glu Asp Thr Ala Val Tyr Tyr Cys
            85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                    245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Phe Arg Val Val
        290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                    325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 24
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr
225                 230
```

<210> SEQ ID NO 25
<211> LENGTH: 327
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Ser Ala Ser Thr Lys Gly Pro Ser Val Phe Pro Leu Ala Pro Cys Ser
1               5                   10                  15

Arg Ser Thr Ser Glu Ser Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Asn Phe Gly Thr Gln
65                  70                  75                  80

Thr Tyr Thr Cys Asn Val Asp His Lys Pro Ser Asn Thr Lys Val Asp
                85                  90                  95
```

```
Lys Thr Val Glu Arg Lys Cys Cys Val Glu Cys Pro Pro Cys Pro Ala
            100                 105                 110

Pro Pro Val Ala Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Phe Arg Val Val Ser Val Leu Thr Val His Gln Asp
            180                 185                 190

Trp Leu Asn Gly Lys Glu Tyr Lys Cys Lys Val Ser Asn Lys Gly Leu
        195                 200                 205

Pro Ala Pro Ile Glu Lys Thr Ile Ser Lys Thr Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Met Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 26
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gacatagtga tgactcaaag tccggacagc ctggcggtgt cactcggcga acgggcaact      60
atcaactgcc gagccagcga gagcgtcgat aattacggca tccccttcat gaactggtat     120
cagcagaagc caggacagcc gcccaagctg cttatctacg ccgcttccaa ccggggatca     180
ggggtgcccg atcgatttag tggaagcggt agtgggaccg atttcacact gaccatcagc     240
tcccttcagg ccgaggatgt ggctgtctat tattgtcagc aatccgagga agtgccgctc     300
acgtttggtc agggaaccaa actggagatc aagcggaccg tagcggcgcc tagtgtcttc     360
atcttcccac cctccgacga acagctgaag tctggcactg cttccgtcgt gtgcctgctc     420
aacaactttt accctagaga ggcaaaagtt caatggaaag tagacaatgc cttgcagtcc     480
gggaactccc aggagtctgt cacagagcag gatagtaagg actcaaccta cagcctgtcc     540
agcacactga ccctctccaa agccgactac gagaagcaca agtgtacgc ttgcgaagtt     600 acgcatcagg ggctgtcctc acccgttaca aaaagttta acagagggga gtgc            654
```

```
<210> SEQ ID NO 27
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser
        115                 120

<210> SEQ ID NO 28
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Ala Leu
        35                  40                  45

Ser Asn Tyr Leu Ile Glu Trp Val Arg Gln Ala Pro Gly Gln Gly Leu
    50                  55                  60

Glu Trp Met Gly Val Ile Thr Pro Gly Ser Gly Thr Ile Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Arg Trp Asp Pro Leu Tyr Tyr Tyr Ala Leu
        115                 120                 125

Glu Tyr Trp Gly Gln Gly Thr Thr Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175
```

-continued

```
Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
        210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Ser Gly Gly Gly Gly Ser Gly Gly Gly Gly Ser
1               5                   10                  15

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Asp Lys Thr His Thr
1               5
```

IL-6 ANTAGONISTS AND USES THEREOF

RELATED APPLICATIONS

The present application is a continuation-in-part of International Application No. PCT/US2013/069279, filed on Nov. 8, 2013, which claims priority to U.S. Application Ser. No. 61/723,972, filed Nov. 8, 2012 and U.S. Application Ser. No. 61/831,699, filed Jun. 6, 2013. The entire content of each of the foregoing applications is hereby incorporated herein by reference.

SEQUENCE LISTING

The instant application contains a Sequence Listing which has been submitted electronically in ASCII format and is hereby incorporated by reference in its entirety. Said ASCII copy, created on Nov. 19, 2014, is named D2046-706230_SL.txt and is 46,378 bytes in size.

FIELD OF THE INVENTION

The field of the invention relates to IL-6. More particularly, the field relates to modulators of IL-6 and their uses in treating disease such diseases of the eye.

BACKGROUND

IL-6 is a pleiotropic cytokine with reported roles in inflammation, hematopoiesis, angiogenesis, cell differentiation, and neuronal survival.

SUMMARY

The invention relates to IL-6 antibodies and fragments, and derivatives of such antibodies and fragments that have certain features, including binding specificity to site II of IL-6, and methods of using such antibodies, fragments, and derivatives. Accordingly, the present invention relates to an antibody, fragment, or derivative thereof that can specifically bind to site II of an IL-6. In some embodiments, the antibody, fragment, or derivative can bind to IL-6 with a $K_D$ of 240 pM or less. In some embodiments, the antibody, fragment, or derivative has a $T_m$ of 70° C. or greater. In some embodiments, the antibody, fragment, or derivative can bind to IL-6 with a $K_D$ of 240 pM or less and has a $T_m$ of 70° C. or greater. The antibody or fragment or derivative thereof can, in some cases, bind to at least one of R24, K27, Y31, D34, S118, or V121 of human IL-6; in some cases the antibody or fragment or derivative thereof can bind to R24, K27, Y31, D34, S118, and V121 of human IL-6. In embodiments, the antibody or fragment or derivative thereof can bind to at least 1, at least 2, at least 3, at least 4, or at least 5 of R24, K27, Y31, D34, S118, and V121 of human IL-6.

In one aspect provided herein is an antibody or fragment thereof (e.g., an antigen binding fragment thereof) that can specifically bind to site II of a human IL-6.

In embodiments, the antibody or fragment thereof (e.g., an antigen binding fragment thereof) can bind to an IL-6 with a $K_D$ of 200 pM or less.

In embodiments, the antibody or fragment thereof (e.g., an antigen binding fragment thereof) can bind to an IL-6 with a $K_D$ of 200 pM or less and/or has a $T_m$ of 70° C. or greater.

In embodiments, the antibody or fragment thereof (e.g., an antigen binding fragment thereof) can bind to an IL-6 with a $K_D$ of 200 pM or less and/or has a $T_m$ of 80° C. or greater.

In embodiments, the antibody or fragment thereof (e.g., an antigen binding fragment thereof) binds to at least one of R24, K27, Y31, D34, S118, and V121 of a human IL-6. In embodiments, the antibody or fragment thereof (e.g., an antigen binding fragment thereof) binds to at least two of R24, K27, Y31, D34, S118, and V121 of a human IL-6. In embodiments, the antibody or fragment thereof (e.g., an antigen binding fragment thereof) binds to at least three of R24, K27, Y31, D34, S118, and V121 of a human IL-6. In embodiments, the antibody or fragment thereof (e.g., an antigen binding fragment thereof) binds to at least four of R24, K27, Y31, D34, S118, and V121 of a human IL-6. In embodiments, the antibody or fragment thereof (e.g., an antigen binding fragment thereof) binds to at least five of R24, K27, Y31, D34, S118, and V121 of a human IL-6. In embodiments, the antibody or fragment thereof (e.g., an antigen binding fragment thereof) binds to R24, K27, Y31, D34, S118, and V121 of human IL-6.

In an aspect provided herein is a an antibody (e.g., an isolated antibody, e.g., an isolated monoclonal antibody) or a fragment thereof (e.g., an antigen binding fragment thereof) that comprises (a) a VH CDR1 as set forth in SEQ ID NO:4, a VH CDR2 as set forth in SEQ ID NO:5, and VH CDR3 as set forth in SEQ ID NO:6; and optionally (b) a VL CDR1 as set forth in SEQ ID NO:7, a VL CDR2 as set forth in SEQ ID NO:8, and a VL CDR3 as set forth in SEQ ID NO:9, wherein the antibody or fragment thereof (e.g., the antigen binding fragment thereof) can specifically bind to a human IL-6. In embodiments, the antibody or fragment thereof comprises heavy chain CDRs VH CDR1, VH CDR2, and VH CDR3 that are identical to the CDR sequences respectively set forth in SEQ ID NO:4, SEQ ID NO:5 and SEQ ID NO:6 or that collectively differ from said CDR sequences by no more than 1, 2, 3, 4, or 5 amino acids. In embodiments, the antibody or fragment thereof comprises light chain CDRs VL CDR1, VL CDR2, and VL CDR3 that are identical to the CDR sequences respectively set forth in SEQ ID NO:7, SEQ ID NO:8, and SEQ ID NO:9 or that collectively differ from said CDR sequences by no more than 1, 2, 3, 4, or 5 amino acids.

In an aspect provided herein is an IL-6 antibody (e.g., an isolated IL-6 antibody) or a fragment thereof (e.g., an antigen binding fragment thereof) that can dissociate from human IL-6 with a $K_D$ of 240 pM or less (e.g., as determined by surface plasmon resonance). In embodiments, the antibody can neutralize IL-6 activity with an IC50 of 255 pM or less, e.g., as determined in an in vitro HEK-Blue™ IL-6 assay.

In an aspect provided herein is an IL-6 antibody ((e.g., an isolated IL-6 antibody) or a fragment (e.g., an antigen binding fragment) thereof, that can competitively inhibit binding to a human IL-6 by an antibody or fragment (e.g., an antigen binding fragment) thereof comprising SEQ ID NO:1 and SEQ ID NO:2 or an antibody or fragment (e.g., an antigen binding fragment) thereof comprising SEQ ID NO:3 and SEQ ID NO:2.

In embodiments, the antibody or fragment thereof (e.g., an antigen binding fragment thereof) has a monovalent Kd of 2 nM or greater at pH 5.5.

In embodiments, the antibody or fragment thereof (e.g., an antigen binding fragment thereof) is an IgG2 antibody.

In embodiments, the antibody or fragment thereof (e.g., an antigen binding fragment thereof) has altered FcRn binding compared to a reference antibody. In embodiments, the FcRn binding is decreased compared to a reference antibody. In embodiments, the Fc domain of the antibody or fragment is altered compared to a reference antibody.

In an aspect provided herein is an IL-6 antibody (an antibody that is capable of binding to an IL-6, e.g., to site II of a human IL-6) or fragment thereof that has a modified Fc domain and exhibits reduced FcRn binding compared to a corresponding antibody having a wild type Fc domain.

In embodiments, the antibody or fragment thereof (e.g., an antigen binding fragment thereof) comprises a mutation at one or more of H311, I254, and H436 of SEQ ID NO:23.

In embodiments, the antibody or fragment thereof (e.g., an antigen binding fragment thereof) comprises a mutation at two or more of H311, D313, I254, and H436 of SEQ ID NO:23.

In embodiments, the antibody or fragment thereof (e.g., an antigen binding fragment thereof) comprises a mutation at three or more of H311, D313, I254, and H436 of SEQ ID NO:23.

In embodiments, the antibody or fragment thereof (e.g., an antigen binding fragment thereof) comprises a mutation at each of H311, D313, I254, and H436 of SEQ ID NO:23.

In embodiments, the antibody or fragment thereof (e.g., an antigen binding fragment thereof) comprises one or more mutations (e.g., 1, 2, 3, or 4 mutations) selected from the group consisting of H311A, H311E, H311N, D313T, I254A, I254R, and H435A.

In embodiments, the antibody or fragment thereof (e.g., an antigen binding fragment thereof) is isolated.

In embodiments, the antibody is a monoclonal antibody or a fragment thereof (e.g., an antigen binding fragment thereof). In embodiments, the antibody is a human monoclonal antibody.

In embodiments, the antibody is an isolated monoclonal antibody or a fragment thereof (e.g., an antigen binding fragment thereof).

In embodiments, the antibody (e.g., the isolated monoclonal antibody) comprises SEQ ID NO:23.

Also provided herein is an antibody or fragment (e.g., an antigen binding fragment) thereof (e.g., an IL-6 antibody or fragment thereof as described herein), or a composition comprising such an antibody or fragment thereof, for use in the treatment of an IL-6 associated disease (e.g., for use in the treatment of a subject, e.g. a human subject, having an IL-6 associated disease). In embodiments, said disease is an ocular disease characterized by an elevated level of IL-6 in the vitreous. In embodiments, said disease is diabetic macular edema (DME), diabetic retinopathy, uveitis, dry eye disease, uveitis, age-related macular degeneration (AMD), proliferative diabetic retinopathy (PDR), retinal vein occlusion (RVO), neuromyelitis optica (NMO), corneal transplant, corneal abrasion, or physical injury to the eye. In embodiments, said disease is DME. In embodiments, said disease is dry eye disease. In embodiments, said disease is dry eye syndrome. In embodiments, said disease is uveitis. In embodiments, said disease is AMD. In embodiments, said disease is PDR. In embodiments, said disease is PDR. In embodiments, said disease is corneal transplant, corneal abrasion, or physical injury to the eye. In embodiments, the antibody or fragment (e.g., the antigen binding fragment) thereof is suitable for delivery to the vitreous of the eye. In embodiments, the antibody or fragment (e.g., the antigen binding fragment) thereof is delivered to the vitreous of the eye.

Also provided herein is a method of treating an IL-6 associated disease, the method comprising administering to a subject an IL-6 antibody or fragment thereof (e.g., an antigen binding fragment thereof), e.g., an IL-6 antibody or fragment thereof as described herein. In embodiments, the IL-6 antibody or fragment thereof (e.g., an antigen binding fragment thereof), is administered in a therapeutically effective amount. In embodiments, the IL-6 associated disease is an ocular disease characterized by an elevated level of IL-6 in the vitreous. In embodiments, the IL-6 associated disease is diabetic macular edema (DME), diabetic retinopathy, uveitis, dry eye syndrome, dry eye disease, uveitis, age-related macular degeneration (AMD), proliferative diabetic retinopathy (PDR), retinal vein occlusion (RVO), neuromyelitis optica (NMO), corneal transplant, corneal abrasion, or physical injury to the eye. In embodiments, the antibody or fragment thereof (e.g., the antigen binding fragment thereof), is suitable for delivery to the vitreous of the eye. In embodiments, the antibody or fragment thereof (e.g., the antigen binding fragment thereof), is delivered to the vitreous of the subject's eye. In embodiments, the IL-6 associated disease is diabetic macular edema and the antibody or fragment thereof is delivered to the vitreous of the subject's eye.

In another aspect provided herein is a vector comprising a sequence encoding an IL-6 antibody or fragment thereof (e.g., an antigen binding fragment thereof) described herein. In embodiments, the vector comprises a sequence encoding SEQ ID NO:4, SEQ ID NO:5, SEQ ID NO:6, SEQ ID NO:7, SEQ ID NO:8, or SEQ ID NO:9.

In another aspect provided herein is a cell that can express the sequence of an IL-6 antibody or fragment thereof (e.g., an antigen binding fragment thereof) described herein. In embodiments, the cell can express one or more of SEQ ID NO:4, SEQ ID NO:5, SEQ ID NO:6, SEQ ID NO:7, SEQ ID NO:8, or SEQ ID NO:9.

In yet another aspect, the invention relates to a method of reducing systemic effects of inhibiting an IL-6 in a subject, the method comprising administering to the subject an antibody or fragment thereof that can inhibit an activity of IL-6 and has reduced Fc activity compared to a corresponding antibody or fragment thereof having a wild type Fc domain. In some cases, the method of reducing systemic effects of inhibiting an IL-6 in a subject including administering to the subject an IL-6 antagonist that has FcRn binding greater than 1 μM, e.g., at low pH such as pH 5.5.

As used herein, the term "antibody" is synonymous with immunoglobulin and is to be understood as commonly known in the art. The term antibody is not limited by any particular method of producing the antibody. For example, the term antibody includes, inter alia, recombinant antibodies, monoclonal antibodies, and polyclonal antibodies. As used herein, an antibody is a tetramer, and unless otherwise disclosed, each is composed of two identical pairs of polypeptide chains, each pair having one light chain and one heavy chain. The amino terminus of each chain comprises a variable region of about 100 to 120 or more amino acids that play a primary role in antigen recognition. The carboxy-terminal portion of each chain comprises a constant region with a primary role in antibody effector function. Classes of human light chains are termed kappa and lambda light chains. Heavy chain classes are mu, delta, gamma, alpha, or epsilon, and define the isotype of an antibody. Antibody isotypes are IgM, IgD, IgG, IgA, and IgE, respectively. Within light and heavy chains, the variable and constant regions are joined by a "J" region of about 12 or more amino acids, with the heavy chain also including a "D" region of about three or more amino acids.

The variable regions of each heavy/light chain pair (VH and VL), respectively, form the antigen binding site. Accordingly, an intact IgG antibody, for example, has two binding sites. Except in bifunctional or bispecific antibodies, the two binding sites are the same.

Variable regions of antibody heavy and light chains exhibit the same general structure of relatively conserved framework regions (FR) joined by three hypervariable regions, also termed complementary determining regions or CDRs. The term "variable" refers to the fact that certain portions of the variable domains differ extensively in sequence among antibodies and are involved in the binding and specificity of each particular antibody for its particular antigen. Variability lies primarily in the CDRs, which are separated by the more highly conserved framework regions (FRs). The assignment of amino acids to each domain is made in accordance with the definitions of Kabat Sequences of Proteins of Immunological Interest (National Institutes of Health, Bethesda, Md. (1987 and 1991)), or Chothia and Lesk, J Mol Biol 196:901-917 (1987); Chothia et al., Nature 342:878-883 (1989), which describe methods known in the art.

"Wild type" can refer to the most prevalent allele or species found in a population or to the antibody obtained from a non-manipulated animal, as compared to an allele or polymorphism, or a variant or derivative obtained by a form of manipulation, such as mutagenesis, use of recombinant methods and so on to change an amino acid of the antigen-binding molecule.

The term "antibody fragment" refers to a portion of an intact or a full-length chain or an antibody, generally the target binding or variable region. Examples of antibody fragments include, but are not limited to, Fab, Fab', F(ab')2 and Fv fragments. A "functional fragment" or "analog of an anti-IL-6 site II antibody" is a fragment that can prevent or substantially reduce the ability of IL-6 to bind to receptor, reduce the ability of IL-6/IL-6R complex to bind to gp130, or reduce the ability of ligand to bind to gp130 or to initiate signaling. As used herein, functional fragment generally is synonymous with, "antibody fragment" and with respect to antibodies, can refer to fragments, such as Fv, Fab, F(ab')2 and so on which can prevent or substantially reduce the ability of IL-6 to bind to a receptor, reduce the ability of IL-6/IL-6R complex to bind to gp130, or to initiate signaling.

A "derivative" of an antibody is a polypeptide that can specifically bind to site II of IL-6 and shares sequence with an IL-6 site II antibody, e.g., shares at least one CDR of an antibody that can specifically bind site II of a human IL-6.

"Compete" means that a first antibody, or fragment thereof can compete for binding with a second antibody or a fragment thereof, such that binding of the first antibody with its epitope is detectably decreased in the presence of the second antibody compared to the binding of the first antibody in the absence of the second antibody. In some cases, the term can also refer to the binding of the second antibody to its epitope which is detectably decreased in the presence of the first antibody. The mechanism of such competition can be via, in non-limiting examples, steric hindrance, conformational change, binding to a common epitope.

The term "percent sequence identity" in the context of nucleic acid sequences means the residues in two sequences that are the same when aligned for maximum correspondence. The length of sequence identity comparison may be over at least about nine nucleotides, for example, at least about 18 nucleotides, at least about 24 nucleotides, at least about 28 nucleotides, at least about 32 nucleotides, at least about 36 nucleotides, or at least about 48 or more nucleotides. Algorithms known in the art can be used to measure nucleotide sequence identity. For example, polynucleotide sequences can be compared using FASTA, Gap or Bestfit (Wisconsin Package Version 10.0, Genetics Computer Group (GCG), Madison, Wis.). FASTA, includes, e.g., the programs FASTA2 and FASTA3, provides alignments and percent sequence identity of the regions of the best overlap between the query and search sequences (Pearson, Methods Enzymol 183:63-98 (1990); Pearson, Methods Mol Biol 132:185-219 (2000); Pearson, Methods Enzymol 266:227-258 (1996); Pearson, J Mol Biol 276:71-84 (1998); incorporated herein by reference). Default parameters for a particular program or algorithm are typically used. For example, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

The term "percent sequence identity" in the context of amino acid sequences means the residues in two sequences that are the same when aligned for maximum correspondence. The length of sequence identity comparison may be over at least about five amino acid residues, for example, at least about 20 amino acid residues, at least about 30 amino acid residues, at least about 50 amino acid residues, at least about 100 amino acid residues, at least about 150 amino acid residues, or at least about 200 or more amino acid residues. Sequence identity for polypeptides is typically measured using sequence analysis software. Algorithms for determination of percent sequence identity are known in the art. For example, amino acid sequences can be compared using FASTA, Gap or Bestfit (Wisconsin Package Version 10.0, Genetics Computer Group (GCG), Madison, Wis.). Protein analysis software matches sequences using measures of similarity assigned to various substitutions, deletions and other modifications, including conservative amino acid substitutions. For example, GCG contains programs such as "Gap" and "Bestfit," which can be used with default parameters as specified by the programs to determine sequence homology or sequence identity between closely related polypeptides, such as homologous polypeptides from different species of organisms or between a wild type protein and an analog thereof. See, e.g., GCG Version 6.1 (University of Wisconsin, Madison, Wis.). Polypeptide sequences also can be compared using FASTA using default or recommended parameters, see GCG Version 6.1. FASTA (e.g., FASTA2 and FASTA3) provides alignments and percent sequence identity of the regions of the best overlap between the query and search sequences (Pearson, Methods Enzymol 183:63-98 (1990); Pearson, Methods Mol Biol 132:185-219 (2000)). Another algorithm that can be used when comparing a sequence to a database containing a large number of sequences from different organisms is the computer program BLAST, e.g., blastp or tblastn, using default parameters as supplied with the programs. See, e.g., Altschul et al., J Mol Biol 215:403-410 (1990); Altschul et al., Nucleic Acids Res 25:3389-402 (1997).

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein can comprise about 50%, 60%, 70%, 80%, 90%, 95%, 98%, or 99% pure; for example, a substantially pure polypeptide or protein is 50%, 60%, 70%, 80%, 90%, 95%, 98%, or 99% pure. Protein purity or homogeneity can be assessed by any appropriate means, such as polyacrylamide gel electrophoresis of a protein sample followed by visualizing one or more bands associated with the protein or polypeptide (e.g., upon staining the gel), size-exclusion HPLC, cation-exchange HPLC, reduced capillary electrophoresis in SDS, peptide mapping, or glycan mapping. Higher resolution can be achieved using methods known in the art, for example, or other means of purification.

The term "substantial similarity" when referring to a nucleic acid or fragment thereof, means that when optimally aligned with appropriate nucleotide insertions or deletions with another nucleic acid (or its complementary strand), there is nucleotide sequence identity in at least about 85%, at least about 90%, and at least about 95%, 96%, 97%, 98% or 99% of the nucleotide bases, for example, 85%, 90%, 95%, 96%, 98%, or 99% sequence identity as measured by any known algorithm of sequence identity, such as FASTA, BLAST or Gap.

As applied to polypeptides, the term "substantial identity" or "substantial similarity" means that two amino acid sequences, when optimally aligned, such as by the programs GAP or BESTFIT using default gap weights as supplied with the programs, share at least about 70%, 75%, 80%, 90%, 95%, 96%, 97%, 98%, or 99% sequence identity; e.g., 70%, 75%, 80%, 90%, 95%, 96%, 97%, 98%, or 99% sequence identity. In certain embodiments, residue positions that are not identical differ by conservative amino acid substitutions.

"Therapeutically effective amount" refers to that amount of a therapeutic agent being administered that will ameliorate at least one sign or symptoms a disease being treated or enhance or improve the prophylactic and or therapeutic effect(s) of another therapy (e.g., another therapeutic agent) useful for treating an IL-6 associated disease. It is understood that the therapeutically effective amount may be administered in multiple doses over a limited amount of time or as a chronic treatment.

"Treat", "treating" and "treatment" refer to a method of ameliorating a signs or symptoms or a disease.

As used herein, the term "disease" includes diseases and disorders.

The entire disclosure of each patent document and scientific article referred to herein, and those patent documents and scientific articles cited thereby, is expressly incorporated by reference herein for all purposes.

Additional features and advantages of the invention are more particularly described below.

DETAILED DESCRIPTION

Figure 1:
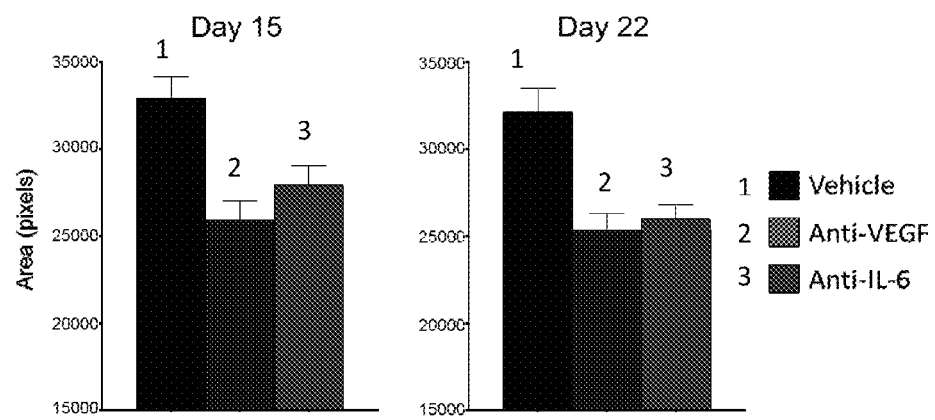
FIG. 1 is a graph illustrating results of an experiment in which an anti-IL-6 antibody was administered IVT in rat CNV model. Anti-VEGF antibody was administered as a positive control and the negative control was vehicle alone. p=0.0054 on Day 15 and p=0.0005 on Day 22 for anti-IL-6 vs. vehicle control.

IL-6 has been implicated as playing a role in a number of diseases such as rheumatoid arthritis, and has been reported to be significantly up-regulated in a number of diseases, including ocular diseases. IL-6 can act via both cis- and trans-mechanisms. In the cis mechanism, it is believed that free IL-6 binds to membrane bound IL-6 receptor (IL-6R is also referred to as IL-6Rα and CD126), and the IL-6/IL-6R complex then interacts with gp130 (also referred to as CD130, oncostatin M receptor, IL-6Rbeta, and IL-6 signal transducer), to activate signaling in the cell containing the complex. In the trans mechanism, free IL-6 binds to soluble IL-6 receptor (sIL-6R). The IL-6/sIL-6R complex can then bind to gp130 present in a cell membrane. A key difference between these mechanisms is that more cell types express gp130 than express IL-6R, whose expression is more limited. Therefore, in diseases for which it is desirable to inhibit IL-6 signaling, for example in those in which it is desirable to broadly inhibit IL-6 signaling, it is useful to inhibit both cis- and trans-IL-6 signaling. Applicants have engineered IL-6 antagonists, e.g., anti-IL-6 antibodies, fragments, and derivatives that can inhibit both cis and trans signaling by IL-6. In addition, applicants have engineered such IL-6 antagonists to achieve enhanced vitreal retention and more rapid systemic clearance.

Features of IL-6 Antagonists (IL-6a)

In general, an IL-6 antagonist (IL-6a) described herein specifically binds to site II (site 2) of an IL-6 and is useful for treatment of IL-6 related eye disease and certain other diseases. An IL-6 related eye disease is one in which an undesirable symptom or biological activity of the disease is associated with the expression or presence of IL-6. In some embodiments the IL-6a has high affinity for both free and bound IL-6, is relatively stable in an organism, can inhibit binding to gp130 of an IL-6 bound to an IL-6R (termed herein an IL-6/IL-6R complex or IL-6/IL-6R), and can have a therapeutic effect. In general, the IL-6a is an antibody or is derived from an antibody. For example, an IL-6a is a high affinity, humanized Fab that can specifically bind to site II of an IL-6 and potently blocks both cis- and trans-IL-6 signaling. In another example, the IL-6a is a full length antibody, e.g., an IgG1 or IgG2 antibody.

In some embodiments, the Fab is also configured as an Fc-engineered sequence or is in a full-length antibody. In some embodiments, the Fc-engineered IL-6a (e.g., the Fc-engineered Fab) has increased vitreal residence time and/or more rapid systemic clearance compared with an appropriate control, e.g., compared with the corresponding antibody, fragment, or derivative thereof that does not have the engineered Fc. These and other features of an IL-6a are further described herein.

Applicants have designed IL-6 antagonists that selectively bind to site II of IL-6 to provide broad inhibition of IL-6 signaling because such molecules can inhibit the binding of gp130 to IL-6, regardless of whether the IL-6 is bound to membrane IL-6R or sIL-6R. Furthermore, targeting the ligand (IL-6) as opposed to the IL-6 receptor can avoid receptor mediated clearance and toxicity due to ADCC (antibody-dependent cell-mediated cytotoxicity). Because IL-6 plays both pathologic and protective roles in disease, use of an IL-6 antagonist (IL-6a) to treat a disease associated with increased IL-6 can improve certain aspects of a condition, but may also cause significant adverse effects, e.g., systemic effects. This duality of IL-6 pathways (i.e., the ability to have desirable and/or undesirable effects) can make it undesirable to treat an IL-6 associated disorder with a systemic inhibitor. Accordingly, the compositions and methods provided herein can be useful for treatments that inhibit at least one IL-6 activity, but do not have an undue effect on positive activities of IL-6, in part because the compositions can be formulated for local delivery, e.g., for local delivery to the eye. For example, in certain aspects, the IL-6a is designed to be of a size suitable for delivery to a particular site. In some embodiments, the IL-6a is a full-length antibody. In some embodiments, the IL-6a is derived from an antibody and is in a format that may have longer residency in the vitreous of the eye and limited systemic leakage. In some embodiments, the IL-6a is a modified antibody (e.g., an antibody with a modified Fc domain) that has longer residency in the vitreous of the eye and/or more limited systemic leakage compared with a corresponding unmodified antibody. In some embodiments, the IL-6a is an IgG2 antibody.

In some aspects, the IL-6a is a relatively small IL-6a such as a fragment of an antibody or other derivative of an antibody that is less than a full length antibody, e.g., a Fab that is derived from an IL-6 antibody. In some cases, an IL-6a is in a format that can pass from one part of a tissue to another with increased kinetics compared to a corresponding full-length IL-6 antibody. In some embodiments, the IL-6a is a Fab that has been engineered to be a larger molecule, which is more likely to have increased residence in the location to which it was delivered compared to the Fab alone, e.g., the IL-6a is dimerized through Fc domain. In certain embodiments, the Fc domain has been engineered such that the Fc moiety has ablated or reduced FcRn binding that can result in extended local residence, e.g., increased vitreal retention and reduce systemic accumulation compared to the same IL-6 binding entity that includes a wild-type Fc.

The IL-6 antagonists described herein also have a sufficiently high affinity for their target, IL-6 to be effective in ameliorating at least one undesirable effect of IL-6. The inhibitors are also sufficiently stable to be useful as therapeutics.

In general, the PK of an IL-6a, e.g., an IL-6a suitable for use in the eye has a PK in the site of delivery, e.g., the vitreous, that is sufficient to provide a therapeutic effect. In non-limiting examples, the PK can be a half-life of at least 12 hours, 24 hours, 2 days, 3 days, 4 days, 5 days, 8 days, 10 days, 14 days, 21 days, 28 days, or 30 days.

Identification of IL-6 Antagonists Binding to Site II

In general, any method known in the art can be used to generate a molecule that can bind to an IL-6, for example, polypeptide libraries or molecular libraries can be screened for candidate compounds in an assay for the ability of a polypeptide or compound to bind to IL-6. Once such a candidate compound is identified, the binding site of the compound can be determined using methods known in the art. For example, a molecule can be tested for the ability to bind to wild type IL-6 and the binding compared to the ability of the compound to bind to an IL-6 mutated in site I, site II, or site III. In embodiments, an IL-6a as described herein retains the ability to bind to an IL-6/IL-6Rα complex and to IL-6, and prevents binding of IL-6/IL-6Rα to gp130. In embodiments, an IL-6a as described herein can compete with gp130 for binding to IL-6/IL-6Rα complex, e.g., by binding to site II of IL-6. Such binding activities can be assayed using methods known in the art.

IL-6a candidates can be tested, for example, using an HEK-Blue™ IL-6 assay system (InvivoGen, San Diego). HEK-Blue™ IL-6 cells are HEK293 cells that are stably transfected with human IL-6R and a STAT3-inducible SEAP reporter gene. In the presence of IL-6, STAT3 is activated and SEAP is secreted. SEAP is assessed using, for example, QUANTI-Blue™ (InvivoGen, San Diego). Addition of an IL-6 antagonist to the cells prevents secretion or decreases the level of SEAP as a result of inhibiting both free and soluble receptor bound IL-6.

$K_D$ refers to the binding affinity equilibrium constant of a particular antibody-antigen interaction or antibody fragment-antigen interaction. An antibody or fragment thereof is said to specifically bind an antigen when the $K_D$ is less than or equal to 250 pM, e.g., less than or equal to 225 pM, 220 pM, 210 pM, 205 pM, 150 pM, 100 pM, 50 pM, 20 pM, 10 pM, or 1 pM. $K_D$ can be determined using methods known in the art, for example using surface plasmon resonance, for example, using the BiaCore™ system.

$K_{off}$ refers to the dissociation rate constant of a particular antibody-antigen interaction or antibody fragment-antigen complex. The dissociation rate constant can be determined using surface plasmon resonance, for example using the BiaCore™ system. A relatively slow $K_{off}$ can contribute to desirable features of a therapeutic, e.g., permitting less frequent administration of the inhibitor to a subject in need of such treatment.

Specificity

A feature of IL-6 antagonists disclosed herein relates to their binding specificity. As discussed supra, IL-6 can be present as free IL-6 and as IL-6 bound to soluble IL-6Rα. Applicants have identified site II of IL-6 as an optimal target for an IL-6 antagonist compared to an inhibitor that that binds to site I of an IL-6. A site I inhibitor may inhibit binding of free IL-6 to IL-6Rα. However, such an inhibitor cannot prevent activity initiated by pre-existing IL-6/IL-6R complexes except by replacement limited by the $K_{off}$ of the complex. Another alternative, an inhibitor that binds to an IL-6Rα, is less suitable because it may have limited ability to prevent IL-6 activity unless it is present in saturating concentrations. Because the amount of IL-6 receptor is generally quite high compared to the amount of IL-6, this approach may require the administration of an undesirably large amount of a composition that inhibits IL-6 activity by binding to the receptor. In embodiments, the IL-6 antagonists described herein (e.g., the antibodies and fragments and derivatives thereof described herein) can block the activity of IL-6 even when IL-6 is bound to IL-6R. Accordingly, an advantage of an IL-6a as described herein is that relatively less of the composition may need to be administered to achieve a therapeutic effect compared to an inhibitor targeting an IL-6 receptor. Anti-receptor antibodies have been reported to be cleared rapidly by receptor mediated clearance significantly limiting their PK, therefore requiring larger doses, more frequent dosing, or both. Additionally, both anti-receptor and anti-site I IL-6 antibodies pose a problem in that they significantly increase the tissue concentration of IL-6 by disrupting the normal receptor mediated clearance pathway of the ligand, thereby exposing the subject to potentially undesirable levels of IL-6 in a tissue. Furthermore, use of an inhibitor targeting IL-6Rα may necessitate the presence of the inhibitor near both sites at which inhibition is sought and a site at which it is not desirable, e.g., systemic treatment. Use of an IL-6a that binds site II, the site to which gp130 binds, permits inhibition via free IL-6 as well as IL-6 that is bound to an IL-6R, but has not yet activated an IL-6 pathway via gp130. Accordingly, the IL-6 antagonists described herein are designed to bind to both forms of IL-6 (soluble and receptor bound), specifically the IL-6 antagonists bind to site II of IL-6, which is accessible in both forms. Compositions containing an IL-6a as described herein can inhibit both cis and trans signaling by IL-6.

In some cases compounds and methods provided herein are designed to provide an effective IL-6 blockade sufficient to treat at least one sign or symptom of an IL-6 associated disorder, for example, inhibiting angiogenesis and/or inflammation.

Compounds described herein are useful for treating eye diseases characterized by an undesirably high level of IL-6, e.g., in the vitreous (see Yuuki et al., J Diabetes Compl 15:257 (2001); Funatsu et al., Ophthalmology 110: 1690, (2003); Oh et al., Curr Eye Res 35:1116 (2010); Noma et al., Eye 22:42 (2008); Kawashima et al., Jpn J Ophthalmol 51:100 (2007); Kauffman et al., Invest Ophthalmol Vis Sci 35:900 (1994); Miao et al., Molec Vis 18:574(2012)).

In general, an IL-6a as described herein is a potent antagonist of IL-6 signaling. This is achieved in part by designing molecules having a high affinity for IL-6, for example, an IC50 less than or equal to 100 pM in an HEK-Blue IL-6 assay using 10 pM IL-6. High affinity of an IL-6a can be determined based on the $K_D$ of the IL-6a, for example, a $K_D$ of less than or equal to 1 nM, less than or equal to 500 pM, less than or equal to 400 pM, less than or equal to 300 pM, less than or equal to 240 pM, or less than or equal to 200 pM.

To produce a biologic IL-6a (e.g., a protein or polypeptide such as an antibody, fragment, or derivative thereof) that is useful for treating a disorder associated with increased IL-6 expression or activity, typically it is desirable that the biologic IL-6a have high productivity. For example, a suitable productivity is greater than or equal to 1 g/L (e.g., greater than or equal to 2 g/L, greater than or equal to 5 g/L, or greater than or equal to 10 g/L).

To effectively administer an IL-6 antagonist, it is necessary that the inhibitor have solubility compatible with the concentration at which it will be administered. For example, in the case of a full-length antibody IL-6a, the solubility is greater than or equal to 20 mg/ml, greater than or equal to 10 mg/ml, greater than or equal to 5 mg/ml, or greater than or equal to 1 mg/ml.

Furthermore, to be a viable treatment, the inhibitor must have high stability at the body temperature of the delivery and activity sites as well as storage stability. For example, a $T_m$ of greater than or equal to 60° C. (e.g., greater than or equal to 60° C., greater than or equal to 62.5° C., greater than or equal to 65° C., greater than or equal to 70° C., greater than or equal to 73° C., greater than or equal to 75° C.) and a $T_{onset}$ of greater than or equal to 45° C., e.g., greater than or equal to 50° C., greater than or equal to 51° C., greater than or equal to 55° C., or greater than or equal to 60° C. Methods of determining the $T_m$ and $T_{onset}$ can be determined using methods known in the art.

Antagonists having the desired features can be selected from suitable types of molecules known in the art, for example antibodies, including fragments and derivatives of an IL-6 site II targeted antibody that generally retains or maintains sufficient features of the parent IL-6 antibody (e.g., desired binding properties). Such antagonists include $F_{ab}$ fragments, scFvs, $F_{ab}$ fragments engineered to include an Fc moiety, and full-length antibodies engineered to have a framework different from the parent IL-6 site II targeted antibody.

In some aspects, the IL-6a disclosed herein comprises a human antibody antigen-binding site that can compete or cross-compete with an antibody or fragment thereof that can bind to site II of IL-6. For example, the antibody or fragment thereof can be composed of a VH domain and a VL domain disclosed herein, and the VH and VL domains comprise a set of CDRs of an IL-6/site II binding antibody disclosed herein.

Any suitable method may be used to determine the domain and/or epitope bound by an IL-6a, for example, by mutating various sites on an IL-6. Those sites in which mutations prevent or decrease binding of the IL-6a and the IL-6 ligand are involved either directly in binding to the IL-6a or indirectly affect the binding site, e.g., by affecting conformation of the IL-6. Other methods can be used to determine the amino acids bound by an IL-6a. For example, a peptide-binding scan can be used, such as a PEPSCAN-based enzyme linked immuno assay (ELISA). In a peptide-binding scan of this type, short overlapping peptides derived from the antigen are systematically screened for binding to a binding member. The peptides can be covalently coupled to a support surface to form an array of peptides. Peptides can be in a linear or constrained conformation. A constrained conformation can be produced using peptides having a terminal cysteine (cys) residue at each end of the peptide sequence. The cys residues can be covalently coupled directly or indirectly to a support surface such that the peptide is held in a looped conformation. Accordingly, a peptide used in the method may have a cys residue added to each end of a peptide sequence corresponding to a fragment of the antigen. Double looped peptides can also be used, in which a cys residue is additionally located at or near the middle of the peptide sequence. The cys residues can be covalently coupled directly or indirectly to a support surface such that the peptides form a double-looped conformation, with one loop on each side of the central cys residue. Peptides can be synthetically generated, and cys residues can therefore be engineered at desired locations, despite not occurring naturally in the IL-6 site II sequence. Optionally, linear and constrained peptides can both be screened in a peptide-binding assay. A peptide-binding scan may involve identifying (e.g., using an ELISA) a set of peptides to which the binding member binds, wherein the peptides have amino acid sequences corresponding to fragments of an IL-6a (e.g., peptides that include about 5, 10, or 15 contiguous residues of an IL-6a), and aligning the peptides in order to determine a footprint of residues bound by the binding member, where the footprint comprises residues common to overlapping peptides. Alternatively or additionally the peptide-binding scan method can be used to identify peptides to which the IL-6a binds with at least a selected signal:noise ratio.

Other methods known in the art can be used to determine the residues bound by an antibody, and/or to confirm peptide-binding scan results, including for example, site directed mutagenesis (e.g., as described herein), hydrogen deuterium exchange, mass spectrometry, NMR, and X-ray crystallography.

Typically, an IL-6a useful as described herein is a human antibody molecule, a humanized antibody molecule, or binding fragment thereof. In general, the antibody is a monoclonal antibody. The origin of such an antibody can be human, murine, rat, camelid, rabbit, ovine, porcine, or bovine and can be generated according to methods known to those in the art.

In general, an IL-6a comprises at least the CDRs of an antibody that can specifically bind to site II of an IL-6 (e.g., a human IL-6). The structure for carrying a CDR or a set of CDRs of the invention can be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains can be determined by reference to Kabat, et al., 1983 (National Institutes of Health), and updates thereof findable under "Kabat" using any internet search engine.

An IL-6a that is an antibody generally comprises an antibody VH domain (e.g., SEQ ID NO:1 or SEQ ID NO:3) and/or VL domain (e.g., SEQ ID NO:2). A VH domain comprises a set of heavy chain CDRs (VHCDRs), and a VL domain comprises a set of light chain CDRs (VLCDRs). Examples of such CDRS are provided in Example 3, examples of which are illustrated in SEQ ID NOs:4-9. An antibody molecule can comprise an antibody VH domain comprising a VHCDR1, VHCDR2 and VHCDR3 and a framework. It can alternatively or also comprise an antibody VL domain comprising a VLCDR1, VLCDR2 and VLCDR3 and a framework.

Disclosed herein are IL-6 antagonists comprising a VHCDR1 and/or VHCDR2 and/or VHCDR3 such as those disclosed herein and/or a VLCDR1 and/or VLCDR2 and/or VLCDR3 such as those disclosed herein. The IL-6a can comprise one or more CDRs of any of the antibodies, fragments or derivatives described herein. The IL-6a can comprise a set of VHCDRs (e.g., VHCDR1, VHCDR2, and VHCDR3), and optionally it can also comprise a set of VLCDRs (e.g., VLCDR1, VLCDR2, and VLCDR3). The CDRs can be derived from one or more antibodies, fragments, or derivatives described herein. For example, the VLCDRs can be derived from the same or a different antibody as the VHCDRs.

In general, a VH domain is paired with a VL domain to provide an antibody antigen-binding site. For example, the HC domain of SEQ ID NO:1 or SEQ ID NO:3 is paired with the LC domain of SEQ ID NO:2. In some cases, a VH or VL domain alone can be used as an IL-6a.

In some aspects, the IL-6a is an antibody molecule, fragment, or derivative thereof that comprises (i) a VH domain sequence that has at least 60, 70, 80, 85, 90, 95, 98 or 99% amino acid sequence identity with a VH domain described herein, e.g., a VH domain of SEQ ID NO:1 or SEQ ID NO:3, or (ii) a set of VHCDRs (e.g., VHCDR1, VHCDR2, and/or VHCDR3) of those sequences (the sequences defined in (i)). In embodiments, the antibody molecule, fragment, or derivative thereof comprises a VHCDR1, VHCDR2, and VHCDR3 of SEQ ID NO:1 or a VHCDR1, VHCDR2, and VHCDR3 of SEQ ID NO:3. In embodiments, the antibody molecule, fragment, or derivative thereof comprises a VHCDR1, VHCDR2, and VHCDR3 that collectively differ from the VHCDR1, VHCDR2, and VHCDR3 of SEQ ID NO:1 by no more than 1, no more than 2, no more than 3, no more than 4, or no more than 5 amino acids. In embodiments, the antibody molecule, fragment, or derivative thereof comprises a VHCDR1, VHCDR2, and VHCDR3 that collectively differ from the VHCDR1, VHCDR2, and VHCDR3 of SEQ ID NO:3 by no more than 1, no more than 2, no more than 3, no more than 4, or no more than 5 amino acids.

The antibody molecule, fragment, or derivative thereof can optionally also comprise (i) a VL domain sequence that has at least 60, 70, 80, 85, 90, 95, 98 or 99% amino acid sequence identity with a VL domain described herein, e.g., a VL domain of SEQ ID NO:2, or (ii) a set of VLCDRs (e.g., VLCDR1, VLCDR2, and/or VLCDR3) of those sequences (the sequences defined in (i)). In embodiments, the antibody molecule, fragment or derivative thereof comprises VLCDR1, VLCDR2, and VLCDR3 of SEQ ID NO:2. In embodiments, the antibody molecule, fragment, or derivative comprises a VLCDR1, VLCDR2, and VLCDR3 that collectively differ from the VLCDR1, VLCDR2, and VLCDR3 of SEQ ID NO:3 by no more than 1, no more than 2, no more than 3, no more than 4, or no more than 5 amino acids. Algorithms that can be used to calculate percent identity of two amino acid sequences include e.g., BLAST, FASTA, or the Smith-Waterman algorithm, e.g., employing default parameters.

An IL-6a as described herein can comprise antibody constant regions or parts thereof, e.g., human antibody constant regions or parts thereof. For example, a VL domain may be attached at its C-terminal end to antibody light chain constant domains including human CK or CL chains. Similarly, an IL-6a based on a VH domain can be attached at its C-terminal end to all or part (e.g., a CH1 domain) of an immunoglobulin heavy chain derived from any antibody isotype, e.g. IgG, IgA, IgE and IgM and any of the isotype sub-classes, particularly IgG1, IgG2, IgG3 and IgG4.

In some cases, an antibody of the invention is further modified using methods known in the art create a sequence having a specific allotype, for example an allotype that predominates in a population having a particular geographic origin. In some cases, the human heavy chain constant region is modified for this purpose.

An IL-6a can be an antibody molecule, binding fragment thereof, or variant, having one or more CDRs, for example, a set of CDRs, within an antibody framework. For example, one or more CDRs or a set of CDRs of an antibody (e.g., an antibody or fragment or derivative thereof as described herein) may be grafted into a framework (e.g., human framework) to provide an antibody molecule. The framework regions can be derived from human germline gene sequences, or be non-germline in origin.

VH and/or VL framework residues can be modified as discussed and exemplified herein e.g., using site-directed mutagenesis.

Amino acid changes can be made in one or more framework regions and/or one or more CDRs derived from an antibody IL-6a targeted to site II of IL-6 (termed herein a "reference IL-6 antibody") using methods and parameters known in the art. Also included herein is a resulting IL-6 antagonist that retains binding to site II of an IL-6 (e.g., site II of a human IL-6) and typically has at least the same binding or increased affinity compared to the reference IL-6 antibody. In some cases, to improve a parameter such as stability, a change that results in a decrease in binding affinity of the derived IL-6a compared to the reference IL-6a (e.g., the reference antibody) can be introduced to create a useful IL-6a. In some embodiments, e.g., in some cases in which the reference relates to FcRn binding or a pharmacokinetic (PK) parameter such as half-life in the vitreous or systemic half-life (e.g., in blood, plasma, serum, lymph, liver, kidney, other tissue, or body fluid), a reference antibody may be an antibody that does not specifically bind an IL-6.

A change in the amino acid sequence of an IL-6a polypeptide can include substituting one or more amino acid residue(s) with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, and N-acetylserine. Those amino acid residues that are derivatized at their N-alpha position will only be located at the N-terminus of an amino-acid sequence. The amino acid is typically an L-amino acid. In some cases the amino acid is a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention can comprise non-natural or non-standard amino acids as discussed herein. Non-standard amino acids (e.g., D-amino acids) can be incorporated into an amino acid sequence using methods known in the art, for example in synthesis of the molecule or by post-synthesis modification or replacement of an amino acid. In some cases, a D-amino acid is used to increase PK of an IL-6a.

Novel VH or VL regions carrying CDR-derived sequences of the invention may be generated using random mutagenesis of one or more selected VH and/or VL nucleic acid sequences to generate mutations within the entire variable domain. For example, error-prone PCR can be used (Chao et al., Nature Protocols, 1:755-768 (2006)). In some embodiments one or two amino acid substitutions are made within an entire variable domain or set of CDRs. Other methods know in the art can be used to generate mutations, for example site-directed mutagenesis, typically in one or more CDRs.

One method for producing an antibody IL-6a, is to alter a VH domain such as those depicted in SEQ ID NO:1 and SEQ ID NO:3 by adding, deleting, substituting or inserting one or more amino acids. The altered VH domain can be combined with a VL domain such as that depicted in SEQ ID NO:2, which can also be altered as described herein and using methods known in the art. Such altered molecules are tested for their ability to bind to site II of IL-6 and optionally for other desired properties such as increased affinity compared to a reference molecule. In some cases, a variant VH or VL domain can have 1, 2, 3, 4, or 5 such alterations (e.g., 1, 2, 3, 4, or 5 amino acid substitutions).

An IL-6a of the invention can be a fragment of an antibody that binds to site II of an IL-6 provided that the fragment comprises an antigen binding site, e.g., can bind to site II of an IL-6. Antibody fragments of the invention are generally obtained starting with a reference (parent) antibody molecule such as an antibody molecule comprising SEQ ID NO:1 and SEQ ID NO:2 or SEQ ID NO:3 and SEQ ID NO:2. Antibody fragments can be generated using methods known in the art such as recombinant DNA, enzymatic cleavage (for example, using pepsin or papain), chemical cleavage of an antibody (for example, chemical reduction of disulfide bridges). Antibody fragments that comprise an antibody antigen-binding site include, but are not limited to, molecules such as Fab, Fab', Fab'-SH, scFv, Fv, dAb, Fd, and disulfide stabilized variable region (dsFv). Various other antibody molecules including one or more antibody antigen-binding sites can be engineered, including for example F(ab')2, F(ab)3, diabodies, triabodies, tetrabodies, and minibodies. Examples of antibody molecules and methods for their construction and use are described in Holliger and Hudson, 2005, Nat Biotechnol 23:1126-1136. Non-limiting examples of binding fragments are a Fab fragment composed of VL, VH, constant light chain domain (CL) and constant heavy chain domain 1 (CH1) domains; an Fd fragment composed of VH and CH1 domains; an Fv fragment composed of the VL and VH domains of a single antibody; a dAb fragment composed of a VH or a VL domain; isolated CDR regions; an F(ab')2 fragment, a bivalent fragment comprising two linked Fab fragments; a single chain Fv molecule (scFv), in which a VH domain and a VL domain are linked by a peptide linker which allows the two domains to associate to form an antigen binding site; a bispecific single chain Fv dimer (for example as disclosed in WO 1993/011161) and a diabody, which is a multivalent or multispecific fragment constructed using gene fusion (for example as disclosed in WO94/13804). Fv, scFv, or diabody molecules can be stabilized by the incorporation of disulfide bridges linking the VH and VL domains. Minibodies comprising an scFv joined to a CH3 domain can also be used as an IL-6a. Other fragments and derivatives of an antibody that can be used as an IL-6a include a Fab', which differs from a Fab fragment by the addition of a few amino acid residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

In some cases, an IL-6a that is an antibody fragment has been chemically modified to improve or introduce a desirable property, for example PEGylation to increase half-life or incorporation.

A dAb (domain antibody) is a small monomeric antigen-binding fragment of an antibody (the variable region of an antibody heavy or light chain. VH dAbs occur naturally in camelids (e.g., camels and llamas) and can be produced by immunizing a camelid with a target antigen, isolating antigen-specific B cells and directly cloning dAb genes from individual B cells. An IL-6a of the present invention can be a dAb comprising a VH or VL domain substantially as set out herein, or a VH or VL domain comprising a set of CDRs substantially as set out herein.

Antibodies of the invention include bispecific antibodies in which two different variable regions are combined in the same molecule. An Il-6a can be incorporated as part of a bispecific antibody prepared using methods known in the art, for example, prepared chemically or from hybrid hybridomas. Such a molecule can be a bispecific antibody fragment of a type discussed above. One non-limiting example of a method for generating a bispecific antibody is BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction. Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, are useful, in part because they can be constructed and expressed in *E. coli*. Diabodies (and many other polypeptides, such as antibody fragments) of appropriate binding specificities can be readily selected using phage display (WO 1994/13804) from libraries. If one arm of the diabody is to be kept constant, for example, with a specificity directed against site II of IL-6, then a library can be made where the other arm is varied and an antibody of appropriate specificity selected.

Bispecific whole antibodies may be made by alternative engineering methods as described in described in WO 1996/27011, WO 1998/50431 and WO 2006/028936.

In some cases, an IL-6a of the invention comprises an antigen-binding site within a non-antibody molecule, for example, by incorporating one or more CDRs e.g. a set of CDRs in a non-antibody protein scaffold, as discussed further below. In some cases, the CDRs are incorporated into a non-antibody scaffold. An IL-6 site II binding site can be provided by an arrangement of CDRs on non-antibody protein scaffolds, such as fibronectin or cytochrome B, or by randomizing or mutating amino acid residues of a loop within a protein scaffold to confer binding specificity for an IL-6 site II. Scaffolds for engineering novel binding sites in proteins are known in the art. For example, protein scaffolds for antibody mimics are disclosed in WO200034784, which describes proteins (antibody mimics) that include a fibronectin type III domain having at least one randomized loop. A suitable scaffold into which to graft one or more CDRs, e.g., a set of HCDRs, can be provided by any domain member of the immunoglobulin gene superfamily. The scaffold can be a human or non-human protein. An advantage of a non-antibody protein scaffold is that it can provide an antigen-binding site in a scaffold molecule that is smaller and/or easier to manufacture than at least some antibody molecules Small size of a binding member may confer useful physiological properties, such as an ability to enter cells, penetrate deep into tissues or reach targets within other structures, or to bind within protein cavities of the target antigen. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g., using the 10th fibronectin type III domain), lipocalins as well as gamma-crystalline and other Affilin™ scaffolds (Scil Proteins, Halle, Germany) Examples of other approaches include synthetic microbodies based on cyclotides—small proteins having intra-molecular disulfide bonds, microproteins (e.g., Versabodies™, Amunix Inc., Mountain View, Calif.) and ankyrin repeat proteins (DARPins, e.g., from Molecular Partners AG, Zurich-Schlieren, Switzerland). Such proteins also include small, engineered protein domains such as, for example, immuno-domains (see for example, U.S. Patent Publication Nos. 2003/082630 and 2003/157561). Immuno-domains contain at least one complementarity determining region (CDR) of an antibody.

An IL-6a can comprise additional amino acids, e.g., to impart to the molecule another functional characteristic in addition to ability to bind antigen.

In some cases, an IL-6a carries a detectable label, or is conjugated to a toxin or a targeting moiety or enzyme (e.g., via a peptidyl bond or linker) For example, an IL-6a can comprise a catalytic site (e.g., in an enzyme domain) as well as an antigen binding site (e.g., binding site for site II of an IL-6), such that the antigen binding site binds to the antigen and thus targets the catalytic site to IL-6 or IL-6/IL-6R complex. The catalytic site can, in some cases, further inhibit a biological function of an IL-6, e.g., by cleavage of the IL-6, IL-6R, or other molecule that is associated with the IL-6a/IL-6 complex.

In some aspects, the invention includes an antibody IL-6a that has been modified compared to a reference antibody to alter, for example, increase, decrease, or eliminate, the biological effect function of the IL-6a. In one example, the Fc region is modified or the parental Fc domain is replaced with a modified Fc domain to alter the pharmacokinetics of the modified IL-6a compared to the unmodified parent. In some embodiments, the IL-6a is engineered to have an IgG2 framework. In other embodiments, the IL-6a in an IgG1 or IgG2 framework has a modified Fc that increases the binding affinity of the IL-6a at pH 6.0 and does not substantially alter the binding affinity at pH 7.0 compared to a parent or other reference IL-6a, or the Fc domain is modified and the IL-6a has an increased half-life compared to a parent or other reference IL-6a.

In some embodiments, an antibody IL-6a is modified to increase complement fixation and complement-dependent cytotoxicity. In other aspects, the antibody IL-6a is modified to increase the ability of the antibody compared to a reference antibody to activate effector cells and participate in antibody-dependent cytotoxicity (ADCC). In some cases, the antibodies as disclosed herein can be modified both to enhance their capability of activating effector cells and participating in antibody-dependent cytotoxicity (ADCC) and to enhance their capability of fixing complement and participating in complement-dependent cytotoxicity (CDC).

In some embodiments, the antibodies disclosed herein are modified to reduce their ability to fix complement and participate in complement-dependent cytotoxicity (CDC). In other embodiments, the antibodies are modified to reduce their ability to activate effector cells and participate in antibody-dependent cytotoxicity (ADCC). In yet other embodiments, an antibody as disclosed herein can be modified both to reduce its ability to activate effector cells and participate in antibody-dependent cytotoxicity (ADCC) and to reduce its ability to fix complement and participate in complement-dependent cytotoxicity (CDC).

It is generally advantageous to avoid frequent delivery of a dose of an IL-6a, for example, when delivered by injection into the eye. To facilitate this feature, in certain embodiments, the half-life at the site of delivery, e.g., the vitreous, of an IL-6a as disclosed herein is at least 4 days, for example, at least 7 days, at least 9 days, at least 11 days, or at least 14 days. In certain embodiments, the mean half-life of an IL-6a is at least 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 25 days, 30 days, 40 days, 50 days, or 60 days. Methods of increasing the half-life of an antibody are known in the art, for example as described in U.S. Pat. No. 6,277,375 and International Publication Nos. WO 1998/23289 and WO 1997/3461. In some embodiments, the half-life of an IL-6a is greater at the target delivery site, e.g., the vitreous, than systemic half-life, e.g., half-life in blood, serum, plasma, lymph, liver, kidney, or other tissue or body fluid).

In another embodiment, the invention provides an article of manufacture including a container. The container includes a composition containing an IL-6a as disclosed herein, and a package insert or label indicating that the composition can be used to treat an IL-6 related disorder. Typically, the composition is an IL-6a in a composition comprising a pharmaceutically acceptable excipient.

In some cases, the invention is a kit comprising a composition containing an IL-6a as disclosed herein, and instructions to administer the composition to a subject in need of treatment.

In embodiments in which a large IL-6a is desirable, e.g., to enhance retention of the IL-6a at or near its site of delivery, a moiety that increases size but does not significantly adversely affect function of the IL-6a (e.g., binding affinity of the IL-6 for IL-6 or IL-6/IL-6R complex) can be associated with the Il-6a. For example, a Fab can be genetically engineered to be expressed as single polypeptides containing a Fab and an Fc moiety.

In embodiments in which a relatively small size for the IL-6a is desirable, fragments of an IL-6 antibody can be used, for example, an scFv or a Fab fragment. An IgG antibody is about 150 kD in size, a Fab is about 50 kD and an scFv is about 25 kD. In some embodiments, an IL-6a as described herein is less than about 50 kD in size. Such an antagonist can be, for example, less than or equal to 50 kD and greater than 10 kD, less than or equal to 50 kD and greater than 20 kD, or less than or equal to 50 kD and greater than or equal to 25 kD.

In some cases, stability of an IL-6 antagonist, e.g., an antibody or other inhibitor having disulfides, is improved by creating variant in which one or more of the disulfide bridges are more stable than in the parent molecule.

Another advantage of certain IL-6a molecules described herein can be the availability of effective molecules having a size suitable for their mode of delivery, site of delivery, or mode of activity. For example, an IL-6a in a Fab format may be used for a topical application. Methods of engineering such molecules are described herein and are known in the art.

Indications/IL-6 Associated Disease

Diseases that can be treated with an IL-6a of the invention include those diseases in which elevated IL-6 is associated with the disease state or as a prerequisite to the disease state. Such diseases include those in which angiogenesis and inflammation driven by IL-6 contribute to disease pathology. This includes diseases in which IL-6 is elevated compared to normal levels, e.g., diseases in which IL-6 is elevated in the vitreous (such as, e.g., diabetic macular edema, diabetic retinopathy, and uveitis) or tissues of the eye. Examples include certain eye diseases including, without limitation, dry eye syndrome, uveitis, age-related macular degeneration (AMD), proliferative diabetic retinopathy (PDR), diabetic macular edema (DME), retinal vein occlusion (RVO), neuromyelitis optica (NMO). Other ocular disorders that can be treated include those caused by trauma such as corneal transplant, corneal abrasion, or other such physical injury to the eye. Accordingly, the invention includes treating a subject having an IL-6 related disease with an IL-6a described herein. In some embodiments, treatment of a subject also includes determining whether the subject has an IL-6 associated disease, and optionally, whether the subject is resistant to other non-IL-6 inhibitory treatments such as steroids or anti-VEGF therapeutics.

One problem with certain antibody-based therapeutics that are effective at a specific locus such as the eye, for example in the vitreous, is adverse effects that result from systemic administration. One solution is to provide therapeutics that can be delivered locally as opposed to systemically as exemplified by molecules described herein. Because some therapeutics that are locally delivered, e.g., to the vitreous, will, to some extent, appear systemically, it is advantageous to design a molecule that will have relatively rapid systemic turnover. Applicants have engineered an example of such a molecule; an IL-6a antibody that is designed for rapid systemic turnover, e.g., compared to the parental molecule or a reference antibody. This was accomplished by modifying FcRn binding of the molecule to reduce FcRn mediated recycling of the IL-6a. A further advantage of such engineering, i.e., reducing FcRn recycling, can be an enhanced vitreal retention by reducing the efflux of antibodies from the vitreous following IVT administration. Accordingly, in some embodiments, an IL-6a having low FcRn binding can decrease dosing frequency.

Diabetic Macular Edema (DME).

Diabetic macular edema (DME) involves occlusion and leakage of retinal blood vessels, causing reduced visual acuity and potentially blindness. Standard treatments for DME include local administration of steroids or anti-VEGF antibodies. However, many patients are refractory to these therapies. The pathogenesis of diabetic macular edema involves components of angiogenesis, inflammation, and oxidative stress. IL-6 is induced by hypoxia and hyperglycemia and can increase vascular inflammation, vascular permeability, and pathologic angiogenesis. IL-6 can directly induce VEGF expression and can promote choroidal neovascularization in animal models. In DME patients, ocular IL-6 levels are positively correlated with macular thickness and disease severity. IL-6 levels are reportedly elevated in patients who fail anti-VEGF therapy while decreasing in anti-VEGF responsive patients. Accordingly, administration of an IL-6a as described herein is useful for treatment of diabetics in combination with an anti-VEGF therapeutic or as an alternative to anti-VEGF treatment, including for patients who do not respond to anti-VEGF therapy. Treatment of macular edema with an IL-6a may also improve safety by removing the need to completely inhibit either mechanism to inhibit the pathology, thus preserving some of the desired, physiological roles of each cytokine. Accordingly, local IL-6a treatment in combination with VEGF inhibition can decrease the dose frequency and reduce adverse effects of treatment.

In DME there are positive correlations between vitreal IL-6 levels and both disease severity and VEGF refractory subjects. Accordingly, an IL-6a as described herein can be used to treat DME subjects who are refractive to steroid therapy, anti-VEGF therapy, or both. In some cases, an IL-6a is used in combination with anti-VEGF therapy or steroid therapy, e.g., to treat DME.

An IL-6a described herein can also be used to treat disorders such as cancer, e.g., prostate cancer, leukemia, multiple myeloma, inflammatory (such as chronic inflammatory proliferative diseases) and autoimmune disease, e.g., rheumatoid arthritis, Castleman's disease (giant or angiofollicular lymph node hyperplasia, lymphoid hamartoma, angiofollicular lymph node hyperplasia), juvenile idiopathic arthritis (including polyarticular juvenile idiopathic arthritis and systemic juvenile idiopathic arthritis), Still's disease (encompassing juvenile idiopathic arthritis and adult onset Still's disease), adult onset Still's disease, amyloid A amyloidosis, polymyalgia rheumatica, remitting seronegative symmetrical synovitis with pitting edema, spondyloarthritides, Behçet's disease (including treatment of ocular manifestations), atherosclerosis, psoriasis, systemic lupus erythematosis, polymyositis (an inflammatory myopathy), relapsing polychondritis, acquired hemophilia A, multiple sclerosis, anemia of inflammation, and Crohn's disease.

IL-6 antagonists are also useful for treatment of certain neurologic diseases, for example, depression, and Alzheimer's disease.

Other diseases that can be treated with an IL-6a described herein include, without limitation, systemic sclerosis, Takayasu arteritis, giant cell arteritis, graft versus host disease, and TNF-receptor-associated periodic syndrome (TRAPS).

Dosing

An IL-6 antibody or fragment thereof can be administered to a subject (e.g., a patient) who expresses, e.g., abnormally high levels of IL-6. The antibody or fragment thereof can be administered once, or can be administered multiple times. The antibody may be administered, for example, from three times daily to once every six months or longer. The administration can be on a schedule such as three times daily, twice daily, once daily, once every two days, once every three days, once weekly, once every two weeks, once every month, once every two months, once every three months and once every six months. The antibody or fragment thereof can be administered continuously via a minipump or other route such as an implantable slow-release capsule or by an encapsulated cell producing the antibody or fragment thereof. The antibody or fragment thereof can be administered via a mucosal, buccal, intranasal, inhalable, intravenous, subcutaneous, intramuscular, parenteral, intraocular, or intratumor route. The antibody or fragment thereof can be administered once, at least twice or for at least the period of time until the condition is treated, palliated or cured. The antibody or fragment thereof generally will be administered for as long as the condition is present. The antibody or fragment thereof, it will generally be administered as part of a pharmaceutical composition as described herein. The dosage of antibody will generally be in the range of 0.1 to 100 mg/kg, 0.5 to 50 mg/kg, 1 to 20 mg/kg, and 1 to 10 mg/kg. The serum concentration of the antibody or fragment thereof can be measured by any suitable method. One feature of certain compounds described herein is that they require relatively infrequent dosing, for example, once per week, twice per week, three times per week, once every four weeks, once every two weeks, once every 8 weeks, once every 12 weeks, once every 16 weeks, once every 32 weeks, once per month, once per two months, once per three months, or once per six months. In some cases the compound is administered on an as needed basis, determined, for example by a subject's condition. It is a feature of the IL-6 antagonists described herein that permits relatively infrequent dosing is the combination of high potency which is accomplished, at least in part, by a slow off rate once bound to an IL-6 and the ability to deliver a relatively high concentration of the compound.

In some cases, the IL-6a is administered as a monotherapy. In other embodiments, the IL-6a is administered concomitantly with methotrexate or other disease modifying anti-arthritic drug.

Generation of Antibodies

An antibody IL-6a or derivative or fragment thereof can be produced using methods known in the art such as monoclonal antibody methodology (e.g., see Kohler and Milstein (1975) Nature 256: 495). Other techniques for producing monoclonal antibodies can also be employed such as viral or oncogenic transformation of B lymphocytes. Chimeric or humanized antibodies can be prepared based on the sequence of a murine monoclonal antibody prepared using methods known in the art. DNA encoding the heavy and light chain immunoglobulins can be obtained from a murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567). To create a humanized antibody, the murine CDR regions can be inserted into a human framework using methods known in the art (see e.g., U.S. Pat. No. 5,225,539, and U.S. Pat. Nos. 5,530,101; 5,585,089; 5,693,762; and 6,180,370).

In embodiments, an IL-6a described herein (e.g., an anti-IL-6 antibody or derivative or fragment thereof) can specifically bind human IL-6. In embodiments, the IL-6a can specifically bind to site II of IL-6 (e.g., site II of human IL-6).

In some embodiments, an IL-6a antibody is a human monoclonal antibody. Such antibodies can be generated using transgenic or transchromosomic mice comprising portions of a human immune system rather than the mouse system. These transgenic and transchromosomic mice include mice referred to herein as the HuMAb Mouse® and KM Mouse®, respectively, and are collectively referred to herein as "human Ig mice" (e.g., See U.S. Pat. Nos. 5,545, 806; 5,569,825; 5,625,126; 5,633,425; 5,789,650; 5,877, 397; 5,661,016; 5,814,318; 5,874,299; and 5,770,429; U.S. Pat. No. 5,545,807; PCT Publication Nos.: WO 92/03918, WO 93/12227, WO 94/25585, WO 97/13852, WO 98/24884 and WO 99/45962; and PCT Publication No. WO 01/14424).

In another aspect, human anti-IL-6 antibodies can be raised using a mouse that carries human immunoglobulin sequences on transgenes and transchomosomes, such as a mouse that carries a human heavy chain transgene and a human light chain transchromosome. Such mice are described in detail in PCT Publication No. WO 02/43478.

Other transgenic animal systems expressing human immunoglobulin genes are available in the art and can be used to raise an antibody IL-6a. For example, an alternative transgenic system referred to as the Xenomouse™ (Abgenix, Inc.) can be used; such mice are described in, for example, U.S. Pat. Nos. 5,939,598; 6,075,181; 6,114,598; 6,150,584; and 6,162,963. Moreover, transchromosomic animal systems expressing human immunoglobulin genes are available in the art and can be used to raise an antibody IL-6a. For example, mice carrying both a human heavy chain transchromosome and a human light chain transchromosome are described in Tomizuka et al. (2000, Proc Natl Acad Sci USA 97:722-727). Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767.

Phage Display Libraries

In some cases, an antibody IL-6a antibody or derivative or fragment thereof is produced in a method that involves synthesizing a library of human antibodies using phage, screening the library with an IL-6, e.g., a human IL-6, or a fragment thereof, isolating phage that bind IL-6, and obtaining the antibody from the phage.

Recombinant human antibody IL-6a can also be isolated by screening a recombinant combinatorial antibody library. In general, the library is a scFv phage display library, generated using human VL and VH cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). Other methods and reagents that can be used in generating and screening antibody display libraries are known in the art (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology 9:1370-1372 (1991); Hay et al., Hum Antibod Hybridomas 3:81-85 (1992); Huse et al., Science 246: 1275-1281 (1989); McCafferty et al., Nature 348:552-554 (1990); Griffiths et al., EMBO J 12:725-734 (1993); Hawkins et al., J Mol Biol 226:889-896 (1992); Clackson et al., Nature 352:624-628 (1991); Gram et al., Proc Natl Acad Sci USA 89:3576-3580 (1992); Garrad et al., Bio/Technology 9:1373-1377 (1991); Hoogenboom et al., Nuc Acid Res 19:4133-4137 (1991); and Barbas et al., Proc Natl Acad Sci USA 88:7978-7982 (1991), all incorporated herein by reference.

In an example for isolating and producing human IL-6 antibodies with the desired characteristics, a human IL-6 antibody is first used to select human heavy and light chain sequences having similar binding activity toward IL-6, using epitope imprinting methods described in PCT Publication No. WO 93/06213, incorporated herein by reference. The antibody libraries used in this method are generally scFv libraries prepared and screened as described in PCT Publication No. WO 92/01047; McCafferty et al., Nature 348: 552-554 (1990); and Griffiths et al., EMBO J 12:725-734 (1993), all incorporated herein by reference.

Once initial human VL and VH domains are selected, "mix and match" experiments are performed, in which different pairs of the initially selected VL and VH segments are screened for IL-6 binding to select preferred VL/VH pair combinations. To select for desirable features of an IL-6a, the VL and/or VH segments of a selected pair can be randomly mutated. This in vitro affinity maturation can be accomplished, for example, by amplifying VH and VL domains using PCR primers complimentary to a CDR of one or both of the selected VH and VL domains, which primers contain a random mixture of the four nucleotide bases at certain positions such that the resultant PCR products encode VH and VL segments into which random mutations have been introduced into the VH and/or VL. Such randomly mutated VH and VL segments can be re-screened for binding to IL-6, e.g., to site II of IL-6.

Following screening and isolation of an antibody IL-6a from a recombinant immunoglobulin display library, nucleic acids encoding the selected antibody can be recovered from the display package (e.g., from the phage genome) and subcloned into other expression vectors using recombinant DNA techniques known in the art. Such antibodies can be further manipulated to produce an antibody fragment such as those described herein.

Pharmacokinetics (PK)

Testing for PK can be performed using methods known in the art. One barrier to determinations requiring the use of an animal, for example determination of PK, is that human IL-6 has less than 50% homology with that of some animals commonly used for such testing. One method of testing PK is therefore to use a transgenic mouse expressing human IL-6. In some embodiments, a non-human primate is used to determine PK.

In some embodiments, an anti-IL6 antibody is mutated to alter its PK, e.g., by altering the pH sensitivity of FcRn binding. A method of obtaining such mutations is described in the Examples. Accordingly, in some embodiments, the IL-6a has altered systemic PK compared to a parental IL-6a or a reference molecule. In some cases, the PK is not altered or is improved in the vitreous. In some embodiments, the IL-6a has the same or increased PK (e.g., an increased half-life) in the vitreous and reduced systemic PK (e.g., as assayed in a circulatory fluid such as blood, plasma, lymph, serum, liver, kidney, other tissue, or other body fluid) compared to a parental IL-6a or a reference molecule.

Models for Testing an IL-6 Antagonist

IL-6 antagonists can be tested in models of disease for IL-6 associated delivery, particularly for the efficacy of treatment and limited deleterious effects on advantageous IL-6 properties. For example, uveitis can be tested in an experimental autoimmune uveitis model in rats or mice (Caspi, Invest Ophthalmol Vis Sci 52:1873; Agarwal et al., 900:443-69, 2012) using interphotoreceptor retinoid-binding protein (IRBP) in complete Freund's adjuvant (CFA) immunization. Other models include those known in the art for dendritic cell-induced uveitis, adoptive transfer of cultured effector T cells, spontaneous EAU in IRBP TCR Tg mice, endotoxin-induced uveitis, autoimmune uveoretinitis (Haruta et al., Invest Ophthalmol Vis Sci 53:3264 (2011); Yoshimura et al., Rheumatology 48:347-354 (2009)). Other model systems that can be used to examine the effects of an IL-6a disease are, for example, a choroidal neovascularization (CNV) model (Izumi-Nagai et al., Am J Pathol 170:6 (2007); Krzystolik et al., Arch Ophthalmol 120:338 (2002)) and diabetic models such as those described in Kern et al. (Animal Models Of Diabetic Complications Consortium (P01 DK57733), Update Report (September 2001-January 2004)). Animal models useful for testing an IL-6a in rheumatoid arthritis are known in the art, e.g., see Asquith et al. (Eur J Immunol 39:2040-4 (2009)) and Kollias et al. (Ann Rheum Dis 70:1357-62 (2011).

Combination Therapies

In some embodiments, an IL-6a is administered in combination with a second therapeutic entity. For example, an IL-6a is administered in a treatment regime that includes a VEGF inhibitor such as ranidizumab. In some embodiments, an IL-6a is administered in a treatment regime that includes a PDGF inhibitor such as an anti-PDGF antibody or anti-PDGF receptor antibody (e.g., imatinib.

Delivery of IL-6 Antagonist

IL-6 antagonist can be delivered locally, either in direct contact with or near a cell or tissue being targeted for IL-6 inhibition. Non-limiting examples of such delivery methods include injection, infusion, or implantation of a substance containing an IL-6 antagonist In some embodiments, the IL-6a composition is administered as an ophthalmic formulation. The methods can comprise administration of the IL-6a composition and an ophthalmically acceptable carrier. In some embodiments, the ophthalmic formulation is a liquid, semi-solid, insert, film, microparticle, or nanoparticle.

In some embodiments, the IL-6a composition is formulated for topical administration, e.g., to the eye. The topical formulation can be a liquid formulation or semi-solid, for example, a topical formulation can include an aqueous solution, an aqueous suspension, an ointment or a gel. An ophthalmic IL-6a formulation can be topically applied to the front of the eye, under the upper eyelid, on the lower eyelid and in the cul-de-sac. Typically, the ophthalmic formulation is sterile. An IL-6a ophthalmic formulation can contain one or more pharmaceutical excipients suitable for the preparation of ophthalmic formulations. Examples of such excipients are preserving agents, buffering agents, chelating agents, antioxidant agents and salts for regulating the osmotic pressure. Ophthalmic formulations, including both ointments and suspensions, typically have a viscosity that is suited for the selected route of administration. In some embodiments, the ophthalmic formulation has a viscosity of from about 1,000 to about 30,000 centipoise.

In some embodiments, the formulation is a liquid formulation comprising a polymer. Such a polymer can be used to improve the bioavailability, raise viscosity, or reduce drainage from the eye of a liquid formulation. Suitable polymers include, but are not limited to, those described in Wagh et al. (Asian J Pharm, 2:12-17, 2008). In non-limiting examples, the polymer is sodium hyaluronase, chitosan, a cyclodextrin (e.g., hydroxypropyl-β-cyclodextrin), polygalactoronic acid, xyloglucan, xanthan gum, gellan gum, a thiomer, a poly (ortho ester) (e.g., Einmahl, Adv Drug Deliv Rev 53:45-73, 2001), or a tamarind seed polysaccharide (e.g., Ghelardi et al., Antimicrob Agents Chemother 48:3396-3401, 2004).

In some embodiments, a formulation comprising a IL-6a composition for ophthalmic delivery can comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

In some embodiments, purified or deionized water is used in the composition. The pH can be adjusted by adding any physiologically and ophthalmically acceptable pH adjusting acids, bases or buffers to within the range of about 5.0 to 8.5, e.g., pH 7.0, pH 7.3, pH, 7.4, or pH 7.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Examples of salts and buffers that can be used in a formulation include citrate/dextrose, sodium bicarbonate, ammonium chloride and mixtures of the aforementioned acids and bases.

In some embodiments, the osmotic pressure of the ophthalmic composition may be from about 10 milliosmolar (mOsM) to about 400 mOsM, for example, 200 to 400 mOsM, or 220 to 370 mOsM. Generally, the osmotic pressure can be adjusted using physiologically and ophthalmically acceptable salts or excipients. In some embodiments, sodium chloride is included in a formulation, for example, sodium chloride is present in a formulation in a concentration ranging from 0.01% to 1% by weight, or from 0.05% to 0.45% by weight, based on the total weight of the composition. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the desired range. In some embodiments, a sugar such as mannitol, dextrose, sorbitol, glucose and the like is also used to adjust osmolality.

In some embodiments, the methods involve forming or supplying a depot of the agent in contact with the external surface of the eye. A depot refers to a source of agent that is not rapidly removed by tears or other eye clearance mechanisms. This allows for continued, sustained high concentrations of agent be present in the fluid on the external surface of the eye by a single application. In some embodiments, the depot can remain for up to eight hours or more. In some embodiments, the ophthalmic depot formulation includes, but is not limited to, aqueous polymeric suspensions, ointments, and solid inserts.

In some embodiments, a semi-solid composition is a liquid formulation that increases in viscosity upon application to the eye, typically due to the presence of a polymer in the liquid formulation for which an increase is viscosity occurs with a change in temperature, pH, or electrolyte concentration. The polymer can be, for example, celluloseacetophthalate, polyacrylic acid, gellan gum, hyaluronase, chitosan, salts of alginic acid (e.g., sodium alginate), or a block copolymer of ethylene oxide and propylene oxide (e.g., Pluronic®, BASF; poloxamer). In some embodiment, the polyacrylic acid is cross-linked acrylic acid (e.g., Carbopol®). In some embodiments, the semi-solid composition comprises a mixture of carbopol and a block copolymer of ethylene oxide and propylene oxide; a mixture of methyl cellulose and hydroxyethyl cellulose; or a mixture of polyethylene glycol and a block copolymer of ethylene oxide and propylene oxide.

In some embodiments, the IL-6a containing ophthalmic formulation is an ointment or gel. In some embodiment, the ophthalmic formulation is an oil-based delivery vehicle. For example, the formulation can comprises a petroleum or lanolin base to which the IL-6a composition is added (for example at 0.1 to 2%), and excipients. Common bases can include, but are not limited to, mineral oil, petrolatum and combinations thereof. In some embodiments, the ointment is applied as a ribbon onto the lower eyelid.

In some cases, the ophthalmic composition is an ophthalmic insert. For example, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the IL-6a composition is dispersed within the matrix or bonded to the polymer matrix. In some embodiments, the agent is slowly released from the matrix through dissolution or hydrolysis of a covalent bond. In some embodiments, the polymer is bio-erodible (soluble) and the dissolution rate thereof can control the release rate of the agent dispersed therein. In another form, the polymer matrix is a biodegradable polymer that breaks down such as by hydrolysis to thereby release the agent bonded thereto or dispersed therein. In further embodiments, the matrix and agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly(dl-lactide-co-glycolide) (PLGA), or a copolymer of any of these. In some cases, the agent is dispersed into the matrix material or dispersed amongst the monomer composition used to make the matrix material prior to polymerization. In some embodiments, the amount of agent is from about 0.1 to about 50%, or from about 2 to about 20%. The biodegradable or bioerodible polymer matrix can be used so that the spent insert does not have to be removed from the eye. As the biodegradable or bioerodible polymer is degraded or dissolved, the agent is released.

In further embodiments, the ophthalmic insert comprises a polymer, including, but are not limited to, those described in Wagh, et al., "Polymers used in ocular dosage form and drug delivery systems", Asian J. Pharm., pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly(dimethylsiloxane), polyethylene oxide, poly(lactide-co-glycolide), poly(2-hydroxyethylmethacrylate), polyvinyl alcohol), or poly(propylene fumarate). In some embodiments, the insert comprises Gelfoam®. In some embodiments, the insert is a polyacrylic acid of 450 kDa-cysteine conjugate.

The insert can comprise a core that contains the IL-6a composition and an outer tube (e.g., as described in U.S. Patent Pub. No. 20040009222). In some cases, the outer tube can be permeable, semi-permeable, or impermeable to the drug. In some embodiments, the core includes a polymer matrix that does not have a significant effect on the rate of IL-6a composition release. In some cases, the outer tube, the polymer matrix of the core, or both is bioerodible. The co-extruded product can be segmented into drug delivery devices. In some embodiments, the device is uncoated so that the respective ends are open, or the device is coated with, for example, a layer that is permeable to the IL-6a composition, semi-permeable to the IL-6a composition, or bioerodible. In certain embodiments, the IL-6a composition and at least one polymer are admixed in powder form.

In some embodiments, the ophthalmic composition is an ophthalmic film. Polymers suitable for such films include, but are not limited to, those described in Wagh, et al. (supra). In some embodiments, the film is a soft-contract lens, for example, a lens composed of copolymers of N,N-diethyl-acrylamide and methacrylic acid cross-linked with ethyleneglycol dimethacrylate.

In certain embodiments, the IL-6a is in an insert that is in a tubular form, and may be segmented.

In some embodiments, the IL-6a composition is formulated in a therapeutically effective amount, coated by or dispersed in a polymer matrix, such that the IL-6a composition is in granular or particulate form. In some embodiments, the IL-6a composition is released from the formulation as drug from the granules dissolves into or within the matrix, diffuses through the matrix, and is released into the surrounding physiological fluid. In some embodiments, the rate of release is limited primarily by the rate of dissolution of the IL-6a composition from the granules/particles into the matrix; the steps of diffusion through the matrix and dispersion into the surrounding fluid are primarily not release-rate-limiting. In certain embodiments, the polymer matrix is non-bioerodible, while in other embodiments it is bioerodible. Exemplary non-bioerodible polymer matrices can be formed from polyurethane, polysilicone, poly(ethylene-co-vinyl acetate) (EVA), polyvinyl alcohol, and derivatives and copolymers thereof. Exemplary bioerodible polymer matrices can be formed from polyanhydride, polylactic acid, polyglycolic acid, polyorthoester, polyalkylcyanoacrylate, and derivatives and copolymers thereof.

In some cases, the IL-6a composition is formulated in a collagenous material. For example, the insert can be a soluble ophthalmic drug insert (e.g., a polymeric oval film that can be introduced in the upper conjuctival sac for drug delivery; an elliptical insert such as OCUSERT® (pilocarpine ocular therapeutic system, developed by Alza Corporation) which is made of ethylene vinyl acetate; Lacrisert®, a rod shaped insert made of cellulose; New Ophthalmic Drug Delivery Systems (NODS), made of poly (vinyl alcohol); or inserts such as those described in Fabrizio (Adv Drug Deliv Rev 16: 95-106, 1998). In some cases, the insert comprises collagen, gelatin, or a polymer, wherein the polymer is selected from polycaprolactone (PCL), an ethylene/vinyl acetate copolymer (EVA), polyalkyl cyanoacrylate, polyurethane, a nylon, poly(dl-lactide-co-glycolide) (PLGA), or a copolymer of any of these. In some cases, the insert is implanted under the upper eyelid. In some cases, the insert is implanted in the posterior segment of the eye, in the choroidal space, or in the sclera. In some embodiments, the insert is implanted intravitreally or sub-retinally. In some embodiments, the insert is injected sub-retinally. Methods of administration and techniques for their preparation are set forth in *Remington's: The Practice of Science of Pharmacy, 20$^{th}$ edition* (Lippincott Williams & Wilkins, 2006), which is incorporated herein by reference in its entirety.

In other embodiments, an insert containing an IL-6a composition provides a sustained release of the agent to the vitreous of the eye. As used herein, "sustained release" means that the composition releases the agent over an extended period of time in a controlled fashion. In some embodiments, the insert releases the agent at a rate such that the aqueous agent concentration remains less than the vitreous agent concentration during the release. In some embodiments, the aqueous agent concentration is from about 0.002 µg/mL to about 0.01 µg/mL or from about 0.01 µg/mL, to about 0.05 µg/mL, or less than about 0.05 µg/mL. In some embodiments, the agent is released at a rate of about 1 µg/day to about 50 µg/day, or from about 1 µg/day to about 10 µg/day. In some embodiments, the insert further comprises an additional therapeutic agent, as detailed above, e.g., fluocinolone acetonide (such as that found in the ophthalmic insert Retisert®).

In some embodiments, the ophthalmic composition comprises microspheres or nanoparticles. In some embodiment, the microspheres comprise gelatin. In some embodiments, the microspheres are injected to the posterior segment of the eye, in the choroidal space, in the sclera, intravitreally or sub-retinally. In some embodiments, the microspheres or nanoparticles comprises a polymer including, but not limited to, those described in Wagh, et al. (Asian J Pharm 2:12-17, 2008). In some embodiments, the polymer is chitosan, a polycarboxylic acid such as polyacrylic acid, albumin particles, hyaluronic acid esters, polyitaconic acid, poly(butyl) cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, an IL-6a composition comprises an ion-exchange resin. In some embodiments, the ion-exchange resin is an inorganic zeolite or synthetic organic resin. In some embodiments, the ion-exchange resin includes, but is not limited to, those described in Wagh, et al., supra, which is incorporated herein by reference in its entirety. In some embodiments, the ion-exchange resin is a partially neutralized polyacrylic acid.

An IL-6a composition can be provided in an aqueous polymeric suspension. In some embodiments, the IL-6a composition or a polymeric suspending agent is suspended in an aqueous medium (e.g., having the properties as described above). Examples of polymeric suspending agents include, but are not limited to, dextrans, polyethylene glycols, polyvinylpyrolidone, polysaccharide gels, Gelrite®, cellulosic polymers like hydroxypropyl methylcellulose, and carboxy-containing polymers such as polymers or copolymers of acrylic acid, as well as other polymeric demulcents. In some embodiments, the polymeric suspending agent is a water swellable, water insoluble polymer, especially a cross-linked carboxy-containing polymer. In some embodiments, the polymeric suspending agent comprises from at least about 90% to about 99.9%, or from about 95% to about 99.9%, by weight based on the total weight of monomers present, of one or more carboxy-containing monoethylenically unsaturated monomers. In some embodiments, the carboxy-containing monoethylenically unsaturated monomer includes acrylic acid, methacrylic acid, ethacrylic acid, methylacrylic acid (crotonic acid), cis-.alpha.-methylcrotonic acid (angelic acid), trans-α-methylcrotonic acid (tiglic acid), α-butylcrotonic acid, .alpha.-phenylacrylic acid, α-benzylacrylic acid, α-cyclohexylacrylic acid, phenylacrylic acid (cinnamic acid), coumaric acid (o-hydroxycinnamic acid), and umbellic acid (p-hydroxycoumaric acid). In some embodiments, the polymer is cross-linked by a polyfunctional crosslinking agent (e.g., a difunctional crosslinking agent). In some embodiments, the crosslinking agent is contained in an amount of from about 0.01% to about 5%, or from about 0.1% to about 5.0%, or from about 0.2% to about 1%, based on the total weight of monomers present. In some embodiments, the crosslinking agents are nonpolyalkenyl polyether difunctional crosslinking monomers such as divinyl glycol, 2,3-dihydroxyhexa-1,5-diene, 2,5-dimethyl-1,5-hexadiene, divinylbenzene, N,N-diallylacrylamide, N,N-diallymethacrylamide; polyalkenyl polyether crosslinking agents containing two or more alkenyl ether groupings per molecule, e.g., alkenyl ether groupings containing terminal $H_2C=C$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; diolefinic non-hydrophilic macromeric crosslinking agents having molecular weights of from about 400 to about 8,000, such as insoluble diacrylates and polyacrylates and methacrylates of diols and polyols, diisocyanate hydroxyalkyl acrylate or methacrylate reaction products of isocyanate terminated prepolymers derived from polyester diols, polyether diols or polysiloxane diols with hydroxyalkyl-methacrylates, and the like.

In some embodiments, the cross-linked polymers are made from a carboxy-containing monoethylenically unsaturated monomer or monomers as the sole monoethylenically unsaturated monomer present, together with a crosslinking agent or agents. In some embodiments, the polymers are ones in which up to about 40%, and preferably from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, and the like (e.g., Mueller et al. U.S. Pat. No. 4,548,990). In some embodiments, the polymers include polycarbophil (Noveon AA-1), Carbopol®, and DuraSite®. In some embodiments, the cross-linked polymers are prepared by suspension or emulsion polymerizing the monomers, using conventional free radical polymerization catalysts, to a dry particle size of not more than about 50 µm in equivalent spherical diameter. In some embodiments, the average dry particle size is from about 1 to about 30 µm, or from about 3 to about 20 µm in equivalent spherical diameter. In some embodiments, the polymer particles are obtained by mechanically milling larger polymer particles. In further embodiments, such polymers will have a molecular weight from about 250,000 to about 4,000,000, and from 3,000,000,000 to 4,000,000,000. In other embodiments, the particles of cross-linked polymer are monodisperse, meaning that they have a particle size distribution such that at least about 80%, about 90% or about 95%, of the particles fall within a µm band of major particle size distribution. In further embodiments, the monodisperse particle size means that there is no more than about 20%, about 10%, or about 5% particles of a size below 1 µm. In some embodiments, the aqueous polymeric suspension comprises from about 0.05 to about 1%, from about 0.1 to about 0.5%, or from about 0.1 to about 0.5%, of the agent and from about 0.1 to about 10%, from about 0.5 to about 6.5%, from about 0.5 to about 2.0%, from about 0.5% to about 1.2%, from about 0.6 to about 0.9%, or from about 0.6 to about 0.8% of a polymeric suspending agent. Although referred to in the singular, it should be understood that one or more species of polymeric suspending agent can be used with the total amount falling within the stated ranges. In one embodiment, the amount of insoluble lightly cross-linked polymer particles, the pH, and the osmotic pressure can be correlated with each other and with the degree of crosslinking to give a composition having a viscosity in the range of from about 500 to about 100,000 centipoise, and preferably from about 1,000 to about 30,000 or about 1,000 to about 10,000 centipoise, as measured at room temperature (about 25° C.) using a Brookfield Digital LVT Viscometer equipped with a number 25 spindle and a 13R small sample adapter at 12 rpm. In some embodiments, the viscosity is from about 10 to about 400 centipoise, from about 10 to about 200 centipoises or from about 10 to about 25 centipoise.

In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid. For instance, when a formulation containing DuraSite® or other similar polyacrylic acid-type polymer is administered to the eye at a pH of less than about 6.7, the polymer may swell upon contact with tear fluid since it has a higher pH (around 7). This gelation or increase in gelation may lead to entrapment of the suspended particles, thereby extending the residence time of the composition in the eye. In some embodiments, the agent is released slowly as the suspended particles dissolve over time. In some embodiments, this delivery route increases patient comfort and increased agent contact time with the eye tissues, thereby increasing the extent of drug absorption and duration of action of the formulation in the eye. The agents contained in these drug delivery systems will be released from the gels at rates that depend on such factors as the drug itself and its physical form, the extent of drug loading and the pH of the system, as well as on any drug delivery adjuvants, such as ion exchange resins compatible with the ocular surface, which may also be present.

In some embodiments, an IL-6 antagonist is provided to a subject using genetic delivery, e.g., local genetic delivery. Such delivery can be via a transient expression system, a stable (e.g., integrated) expression system such as a lentiviral delivery system manufactured by Bluebird Bio (Cambridge, Mass.), or delivery in a cell factory such as those manufactured by Neurotech (Cumberland, R.I.).

All technical features can be individually combined in all possible combinations of such features.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

The following non-limiting examples further illustrate embodiments of the inventions described herein.

Example 1

Validation of Local IL-6 Blockade in Choroidal Neovascularization (CNV) Model To determine whether local IL-6 blockade could be effective for treating eye disease, e.g., diabetic macular edema (DME) or wet AMD, an anti-IL-6 antibody was locally administered using a model system for choroidal neovascularization. A laser-induced CNV model (eyecro.com/in-vivo/laser-induced-choroidal-neovascularization-cnv/) reproduces many of the pathologic processes underlying DME including inflammation and angiogenesis. Studies were performed in rats at EyeCRO (Oklahoma City, Okla.). Six animals in each group underwent bilateral laser treatment on Day 0 to produce three lesions per eye. On days 3 and 10, 3 µg of a polyclonal anti-rat-IL-6 antibody (R&D Systems AF506; Minneapolis, Minn.) was administered to the test group by intravitreal (IVT) injection, while PBS or an anti-VEGF polyclonal antibody (R&D Systems AF564) was administered to the vehicle and positive control groups, respectively. In vivo angiography was performed on days 15 and 22 to measure the lesion area. On both days 15 and 22, the anti-IL-6 treated group had significantly reduced neovascularization compared to the vehicle control. There was no significant difference in response between the anti-IL-6 treated group and the anti-VEGF positive control. FIG. 1 shows the results of such an experiment. These data demonstrate that an IL-6a, e.g., an anti-IL6 antibody, administered IVT can reduce neovascularization in a rat CNV model to similar levels as an anti-VEGF positive control (p=0.0054 on Day 15 and p=0.0005 on Day 22 for anti-IL-6 vs. vehicle control).

These data indicate that local blockade of IL-6 can be useful for treating eye disease such as diseases involving vascular leakage, e.g., macular edema.

Example 2

Candidate Antibody IL-6 Antagonists

Candidate antibody IL-6 antagonists were developed using a process that first involved immunizations. Immunizations were performed at the direction of the inventors by a contract research organization (CRO). Five BALB/C mice were injected subcutaneously with 80 µg human IL-6 (R&D Systems, cat #206-IL/CF, Minneapolis, Minn.) in PBS containing 1 M NaCl with Freud's adjuvant. Two boosts were performed with 80 µg and 50 µg IL-6. Spleen cells were harvested from the highest titer mouse and fused with P3x763Ag8.653 myeloma cells to form hybridomas.

Hybridoma supernatants were screened for IL-6 binding and antagonism. For the binding ELISA, Costar 9018 plates were coated with 1 µg/mL human IL-6 in PBS overnight at 4° C. Wells were blocked with PBS containing 2% BSA, washed, and then incubated with 50 µL of each hybridoma supernatant diluted 1:2 with PBS containing 2% BSA. After 60 minutes, wells were washed three times with 300 µl PBS containing 0.1% Tween-20. Anti-mouse-HRP diluted 1:3000 in PBS-BSA was then added to each well and incubated for 30 minutes. Wells were washed as above then 3,3',5,5'-tetramethylbenzidine (TMB) substrate was added and the signal measured at 450 and 550 nm. For antagonism studies, HEK-Blue™-IL6 reporter cells (InvivoGen, San Diego, Calif.) were incubated with increasing concentrations of human IL-6 in the presence of 1:10 diluted hybridoma supernatant After 20-24 hours, 20 µl of supernatant was mixed with 180 µl QuantiBlue™ (InvivoGen) and the absorbance measured at 655 nm.

Figure 2:
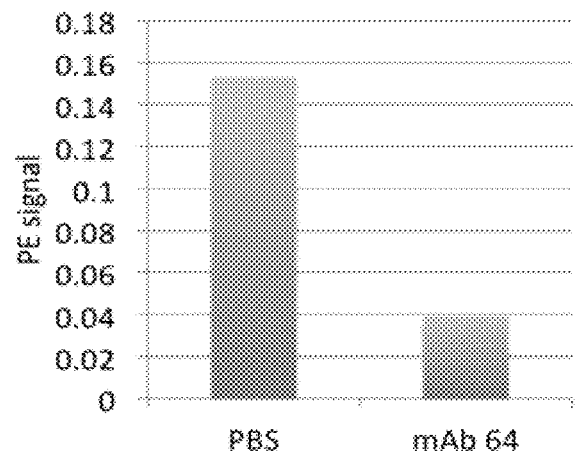
FIG. 2 is a graph illustrating results of a binding experiment testing the ability of the murine 64 antibody to inhibit binding of IL-6/IL-6R to gp130.

Based on binding and antagonism studies, hybridoma 64 was selected by applicants as a lead and subcloned at the CRO. Hybridoma 64 (a murine monoclonal) was further tested for the ability to inhibit binding of IL-6/IL-6Rα complex to gp130 using an enzyme-linked immunosorbant assay (ELISA). Hybridoma 64 at a concentration of 1.5 µg/ml significantly reduced binding of an IL-6/IL-6Rα complex to immobilized gp130 by ELISA (FIG. 2).

The subclones were rescreened and the variable domains of subclone 64.58 were amplified by 5' RACE PCR and sequenced. The mouse variable domain sequences (referred to as m64) are as follows:

m64 VH (variable heavy chain)
(SEQ ID NO: 13)
QVQLQQSGAELVRPGTSVKVSCKASGYAFSNYLIEWVKQRPGQGLEW
IGVITPGSGTINYNEKFKGKAVLTADKSSSTVYMQLSSLTSDDSAVY
FCAKSRWDPLYYYALEYWGQGTSVTVSS m64 VL (variable light chain)
(SEQ ID NO: 14)
DIVLTQSPASLAVSLGQRATISCRASESVDNYGISFMNWFQQKPGQP
PKLLIYAASNQGSGVPARFSGSGSGTDFSLNIHPMEEDDTAMYFCQQ
SKEVPLTFGAGTKLELK To create humanized sequences, the m64 complementarity determining regions (CDRs) were grafted into a human germline framework selected for similarity to the mouse sequence by a computational algorithm. The humanized sequences (referred to as h64) were as follows (altered residues compared to the m64 sequences are underlined) and have about 79.5% identity (VH) and 84.4% identity (VL) with the murine sequences:

h64 VH
(SEQ ID NO: 15)
QVQL<u>VQ</u>SGAE<u>VKK</u>PG<u>SS</u>VKVSCKASGYAFSNYLIEWV<u>RQAP</u>GQGLEW
<u>M</u>GVITPGSGTINY<u>AQKFQGRVT</u>ITADES<u>TS</u>TA<u>Y</u>MELSSL<u>RS</u>ED<u>T</u>AVY
<u>YCAR</u>SRWDPLYYYALEYWGQGT<u>T</u>VTVSS h64 VL
(SEQ ID NO: 16)
DIV<u>M</u>TQSP<u>DS</u>LAVSLG<u>E</u>RATI<u>N</u>CRASESVDNYGISFMNW<u>YQ</u>QKPGQP
PKLLIYAASNQGSGVP<u>D</u>RFSGSGSGTDF<u>TLTI</u>SSL<u>Q</u>AED<u>V</u>A<u>V</u>Y<u>Y</u>CQQ
SKEVPLTFG<u>Q</u>GTKLE<u>I</u>K

The humanized sequences were synthesized by DNA2.0 (Menlo Park, Calif.), then cloned into pcDNA3.1-derived expression vectors as inline fusions with the human IgG1 constant domains. IgGs were expressed by transient transfection in Freestyle™-293 cells (Invitrogen, Grand Island, N.Y.) and purified by protein-A chromatography. In both binding and antagonism studies, the h64 IgG demonstrated considerably reduced potency compared to its m64 predecessor. Therefore, yeast display was utilized to restore the lost affinity.

To carry out the affinity maturation designed to restore or improve the affinity of the humanized h64IgG, the h64 antibody sequences were recloned to generate a Fab molecule in pYC2/CT-derived yeast vectors in which the FabH chain was fused to the anti-FITC scFv 4m5.3 through a (G4S)3 linker (SEQ ID NO: 29). A library of h64 variants was then generated by error prone PCR following the protocol of Chao et al. (2006, Nature Protocols, 1:755-768). H64 variants were expressed and surface captured by yeast labeled with FITC-PEG-NHS then incubated with biotinylated human IL-6. Bound IL-6 was detected with streptavidin-APC, and cells with the highest amount of bound IL-6 relative to the amount of displayed Fabs were selected on a BD FACSAria™ cell sorter. After four rounds of selection, a population of higher affinity variants was selected and sequenced. The sequence of the clone selected by affinity maturation (referred to as h64-1.4) is as follows with the selected mutations (i.e., mutated compared to the sequences of h64 VH and VL) in boldface and the CDRs are underlined. These are the variable domains of 018 (as well as the 020 and 029 IL-6a molecules described below). Note that the full Fabs include the CK and IgG1 CH1 domains. In the context of this application, reference to a "Fab" heavy chain or light chain amino acid sequence means that sequence can be part of a functioning Fab consisting of a light chain-derived sequence and a heavy chain-derived sequence.

h64-1.4 VH (018VH)(variable domain)
(SEQ ID NO: 17)
QVQLVQSGAEVKKPGSSVKVSCKAS<u>GYALSNYLI</u>EWVRQAPGQGLEW
MG<u>VITPGSGTIN</u>YAQKFQGRVTITADESTSTAYMELSSLRSEDTAVY
YCAR<u>SRWDPLYYYALEY</u>WGQGTTVTVSS h64-1.4 VL (018VL)(variable domain)
(SEQ ID NO: 18)
DIVMTQSPDSLAVSLGERATINC<u>RASESVDNYGIPFMN</u>WYQQKPGQP
PKLLIY<u>AASNRGS</u>GVPDRFSGSGSGTDFTLTISSLQAEDVAVYYC<u>QQ
SEEVPLT</u>FGQGTKLEIKRTV The h64-1.4 variable domains were recloned into the pcDNA3.1 human IgG1 vector and expressed as a full length IgG1 in Freestyle™-HEK293 cells (Life Technologies). The resulting purified IgG was significantly more potent than the original h64 antibody in both binding and cellular antagonism studies. Testing affinity using the yeast system, the affinity increased from 343 pM for the original humanized molecule to 43 pM. The antagonist potency was about a ten-fold increase as assayed using the HEK-Blue cell system.

The h64-1.4 IgG was reformatted as a Fab for use in ocular and other indications. Additionally, another round of library generation and yeast based selections was performed to further improve affinity. After four rounds of selection, there was significant enrichment for a VH variant with the A79V mutation. Antibodies, variants and fragments thereof comprising the A79V variant are referred to as 019 IL-6a antibodies, variants, and fragments thereof.

Example 3

Format Selection

To investigate suitable formats for an antibody-based IL-6 antagonist, IL-6 antibodies selected as described supra were tested for transient expression, stability, aggregation properties, binding affinity, and IC50 using Fab, scFv($V_H$-$V_L$) and scFv($V_L$-$V_H$) forms of the 018 sequences.

Results of these studies for one of the candidate IL-6a molecules (sequences containing the 018 variable region) are shown in Table 1.

TABLE 1

| Parameter | Fab | scFv ($V_H$-$V_L$) | scFv ($V_L$-$V_H$) |
| --- | --- | --- | --- |
| Transient expression | 45 mg/ml | 2 mg/L | 4 mg/L |
| Stability ($T_M$) | 73° C. | 43° C. | 46° C. |
| Aggregation (SEC, MALS) | No | Yes | N/A |
| Binding affinity ($K_D$) | 240 pM | 1 nM | 720 pM |
| IC50 with 10 pM IL-6 | 255 pM | 160 pM | 125 pM |

These data demonstrate a method of identifying key features of various formats of an antibody-based IL-6 antagonist and illustrates that for IL-6 antagonists containing the 018 variable regions, the 018Fab format has the most favorable features in most key categories, i.e., expression, stability, aggregation, and binding affinity compared to an scFv configuration. The IC50 of the 018 Fab falls within a reasonable range for therapeutic use.

Example 4

Examples of IL-6a Antibodies, Fragments, and Derivatives

Applicants have identified the following sequences using methods described herein. Underlined sequences represent CDRs of the heavy and light chains. Other sequences can be found throughout the specification.

018 Heavy Chain (Full Length; fl018HC) Polypeptide Sequence in an IgG1 Framework (SEQ ID NO: 19)
QVQLVQSGAEVKKPGSSVKVSCKAS<u>GYALSNYLI</u>EWVRQAPGQGLEW MG<u>VITPGSGTIN</u>YAQKFQGRVTITADESTSTAYMELSSLRSEDTAVY YCAR<u>SRWDPLYYYALEY</u>WGQGTTVTVSSASTKGPSVFPLAPSSKSTS

GGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCP

APELLGGPSVFLFPPKPKDTLMISRTPEVTCVVVDVSHEDPEVKFNW

YVDGVEVHNAKTKPREEQYNSTYRVVSVLTVLHQDWLNGKEYKCKVS

NKALPAPIEKTISKAKGQPREPQVYTLPPSRDELTKNQVSLTCLVKG

FYPSDIAVEWESNGQPENNYKTTPPVLDSDGSEFLYSKLTVDKSRWQ

QGNVFSCSVMHEALHNHYTQKSLSLSPGK

018 Heavy Chain (Full Length; fl018HC) Nucleic Acid Sequence in an IgG1 Framework (SEQ ID NO: 20)
CAAGTGCAGCTGGTGCAGTCAGGGGCCGAGGTTAAGAAGCCAGGGAGCA

GCGTCAAGGTATCTTGTAAAGCGTCTGGTTACGCCCTTTCAAACTACCT

GATCGAATGGGTGAGGCAGGCTCCCGGCCAAGGCCTGGAATGGATGGGA

GTTATCACCCCTGGGAGCGGCACCATTAATTACGCCCAGAAATTTCAGG

-continued
```
GACGAGTGACGATTACCGCCGACGAGTCCACCAGTACTGCCTACATGGA

GCTGTCCTCACTCCGCAGCGAGGACACGGCAGTTTACTACTGCGCCCGG

AGTCGATGGGACCCTCTTTACTATTATGCTCTGGAATACTGGGGCCAGG

GAACGACCGTTACAGTGTCATCTGCTAGCACAAAAGGACCATCAGTCTT

CCCACTTGCTCCTTCATCTAAGAGCACAAGTGGTGGCACTGCAGCCCTT

GGCTGCCTGGTGAAAGATTATTTCCCCGAACCTGTTACAGTTTCTTGGA

ACTCCGGTGCACTGACATCCGGAGTACACACTTTCCCAGCTGTGCTGCA

GAGCTCAGGACTGTATAGCCTGTCTTCGGTGGTCACTGTTCCATCGTCG

AGTCTTGGCACACAGACATATATTTGCAACGTCAATCACAAGCCCTCCA

ACACAAAAGTGGATAAGAAGGTCGAGCCCAAATCTTGTGACAAGACCCA

TACGTGTCCTCCCTGTCCCGCCCCTGAACTGCTGGGAGGCCCTTCTGTG

TTCCTGTTCCCACCTAAGCCAAAGGACACTCTGATGATCAGCCGGACTC

CCGAGGTTACCTGTGTGGTGGTGGATGTGTCTCATGAAGACCCTGAGGT

TAAGTTCAATTGGTACGTGGATGGCGTCGAGGTGCATAACGCAAAAACC

AAGCCGAGAGAGGAGCAGTACaatAGCACCTATAGAGTAGTGAGCGTCC

TGACTGTCTTACATCAGGATTGGCTCAATGGTAAAGAATATAAGTGCAA

GGTAAGCAACAAGGCCCTACCCGCACCAATAGAGAAGACCATCTCCAAG

GCGAAAGGTCAGCCCAGGGAGCCCCAGGTTTATACACTGCCTCCCTCAC

GCGACGAATTAACAAAGAATCAGGTGTCTCTCACCTGTCTCGTCAAGGG

CTTTTACCCTTCCGACATCGCCGTGGAGTGGGAATCCAATGGCCAGCCT

GAGAACAATTATAAGACAACTCCCCCAGTCCTGGATTCAGATGGGTCGT

TCTTTCTATATAGTAAGTTGACCGTGGATAAGTCTCGCTGGCAACAGGG

GAACGTGTTCTCTTGCTCTGTTATGCATGAAGCGCTGCACAATCATTAT

ACCCAGAAGTCCCTGTCCCTGAGCCCCGGGAAG
```

018 Fab Heavy Chain (018FabHC) Polypeptide Sequence in an IgG1 Framework. CDRs are Underlined

```
                                            (SEQ ID NO: 1)
QVQLVQSGAEVKKPGSSVKVSCKASGYALSNYLIEWVRQAPGQGLEWMG

VITPGSGTINYAQKFQGRVTITADESTSTAYMELSSLRSEDTAVYYCAR

SRWDPLYYYALEYWGQGTTVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSC
```

018 Full Length Light Chain (fl018LC) Polypeptide Sequence. CDRs are Underlined

```
                                            (SEQ ID NO: 2)
DIVMTQSPDS LAVSLGERAT INCRASESVD NYGIPFMNWY

QQKPGQPPKL LIYAASNRGS GVPDRFSGSG SGTDFTLTIS

SLQAEDVAVY YCQQSEEVPL TFGQGTKLEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

This is also the light chain sequence for 020 and 029 IL-6 antagonists

018 Full Length Light Chain (018LC) Nucleic Acid Sequence in an IgG1 Framework

```
                                            (SEQ ID NO: 26)
GACATAGTGA TGACTCAAAG TCCGGACAGC CTGGCGGTGT

CACTCGGCGA ACGGGCAACT ATCAACTGCC GAGCCAGCGA

GAGCGTCGAT AATTACGGCA TCCCCTTCAT GAACTGGTAT

CAGCAGAAGC CAGGACAGCC GCCCAAGCTG CTTATCTACG

CCGCTTCCAA CCGGGGATCA GGGGTGCCCG ATCGATTTAG

TGGAAGCGGT AGTGGGACCG ATTTCACACT GACCATCAGC

TCCCTTCAGG CCGAGGATGT GGCTGTCTAT TATTGTCAGC

AATCCGAGGA AGTGCCGCTC ACGTTTGGTC AGGGAACCAA

ACTGGAGATC AAGCGGACCG TAGCGGCGCC TAGTGTCTTC

ATCTTCCCAC CCTCCGACGA ACAGCTGAAG TCTGGCACTG

CTTCCGTCGT GTGCCTGCTC AACAACTTTT ACCCTAGAGA

GGCAAAAGTT CAATGGAAAG TAGACAATGC CTTGCAGTCC

GGGAACTCCC AGGAGTCTGT CACAGAGCAG GATAGTAAGG

ACTCAACCTA CAGCCTGTCC AGCACACTGA CCCTCTCCAA

AGCCGACTAC GAGAAGCACA AAGTGTACGC TTGCGAAGTT

ACGCATCAGG GGCTGTCCTC ACCCGTTACA AAAAGTTTTA

ACAGAGGGGA GTGC
```

019 Fab Heavy Chain (019FabHC, Same Sequence as 018FabHC Except for A79V (Bold/Italic)

```
                                            (SEQ ID NO: 3)
QVQLVQSGAE VKKPGSSVKV SCKASGYALS NYLIEWVRQA

PGQGLEWMGV ITPGSGTINY AQKFQGRVTI TADESTST VY

MELSSLRSED TAVYYCARSR WDPLYYYALE YWGQGTTVTV

SSASTKGPSV FPLAPSSKST SGGTAALGCL VKDYFPEPVT

VSWNSGALTS GVHTFPAVLQ SSGLYSLSSV VTVPSSSLGT

QTYICNVNHK PSNTKVDKKV EPKSC
```

019 VH (Variable Region/019HC, Same Sequence as 018HC Variable Region Except for A79V (Bold/Italic)

```
                                            (SEQ ID NO: 27)
QVQLVQSGAE VKKPGSSVKV SCKASGYALS NYLIEWVRQA

PGQGLEWMGV ITPGSGTINY AQKFQGRVTI TADESTST VY

MELSSLRSED TAVYYCARSR WDPLYYYALE YWGQGTTVTV

SS
```

The 019 Antibody Light Chain (019LC) Sequence (Polypeptide and Nucleic Acid) is the Same as the 018LC

```
CDR1 of 018HC (VH CDR1 018):
                                            (SEQ ID NO: 4)
GYALSNYLIE
```

-continued

CDR2 of 018HC (VH CDR2 018):
(SEQ ID NO: 5)
VITPGSGTIN

CDR3 of 018HC (VH CDR3 018):
(SEQ ID NO: 6)
SRWDPLYYYALEY

CDR1 of 018LC (VL CDR1):
(SEQ ID NO: 7)
RASESVDNYGIPFMN

CDR2 of 018LC (VL CDR2):
(SEQ ID NO: 8)
AASNRGS

CDR3 of 018LC (VL CDR3):
(SEQ ID NO: 9)
QQSEEVPLT

CDR1 of 019HC (VH CDR1 019):
(SEQ ID NO: 4)
GYALSNYLIE

CDR2 of 019HC (VH CDR2 019):
(SEQ ID NO: 5)
VITPGSGTIN

CDR3 of 019HC (VH CDR3 019):
(SEQ ID NO: 6)
SRWDPLYYYALEY

Example 5

Epitope and Structure Mapping

Epitope Mapping

Functional epitope mapping was performed on selected candidate IL-6 antagonists. It was found that a candidate antibody (murine 64 antibody) did not reduce binding of IL-6Rα to IL-6 in an ELISA indicating that the candidate antibody is not binding to site I. Additional experiments were conducted demonstrating that chimeric murine 64 antibody reduced binding of IL-6/IL-6Rα complex to gp130 in an ELISA indicating that either Site II or Site III of IL-6 harbored the binding site for the antibody. It was also found that murine 64 antibody did not significantly block binding of a known site III binding antibody AH-65 (Immunotech, Marseille, France) to IL-6 indicating that the candidate antibody binds site II of IL-6. These data demonstrate that antibodies against site II can be generated and demonstrates a method of identifying such antibodies.

To further define the epitope, mutations in IL-6 were generated in yeast as fusions to 4m5.3 (Boder et al., 2000, Proc Natl Acad Sci USA 97, 10701-10705; Chao et al., 2006, Nat Protoc 1, 755-768). The mutations expressed were in human IL-6 with the following single or double mutations: R24E/D27E, R30E, Y31E, D34R, S118R/V121E, W157E, Q159E/T162P, K171E, and R179E. The expressed mutated IL-6 molecules were used in binding studies with 018 (Fab). Reduced affinity for 018 (Fab) was observed for R24E/K27E, Y31E, D34R, and S118R/V121R, all of which are located in site II of IL-6. Accordingly, the invention described herein includes an antibody that binds to at least one, two, three, four, five, or six of the amino acids at position 24, 27, 31, 34, 118, and 121 of human IL-6 or the equivalent site in an IL-6.

Structural Definition of a Site II Epitope

The following distances were calculated to structurally define site II. The calculations are based on the IL-6/IL-6α/gp130 hexameric crystal structure, PDB 1P9M (Boulanger et al., 2003, Science 300: 2101-2104). Helix 1 of IL-6 runs between site I and site II resulting in certain residues that fall close to site II but have side chains that point toward site I, e.g., R30. D2 and D3 refer to extracellular domains of IL-6Rα.

The following amino acids of IL-6 were determined to fall within 5 Å of gp130-D2-D3: L19, R24, K27, Q28, R30, Y31, D34, E110, Q111, R113, A114, M117, S118, V121, Q124, F125, and K128

The following amino acids were determined to fall within 7 Å of 130-D2-D3: L19, E23, R24, I25, K27, Q28, I29, R30, Y31, D34, K41, Q102, E109, E110, Q111, A112, R113, A114, V115, Q116, M117, S118, K120, V121, L122, Q124, F125, and K128.

Accordingly, a molecule, e.g., an antibody or fragment thereof that can bind one or more of the IL-6 amino acids falling within 5 Å or 7 Å of site II can be an IL-6a.

The sequence of human IL-6 is provided below for reference (underlined sequence is the leader sequence). Amino acids within 7 Å of 130-D2-D3 are in italics. The amino acid numbering, e.g., mutations used to define epitopes, is without the leader sequence:

Human IL-6
(SEQ ID NO: 21)
MNSFSTSAFGPVAFSLGLLLVLPAAFPAPVPPGEDSKDVAAPHRQPLTS

SERIDKQIRYILDGISALRKETCNKSNMCESSKEALAENNLNLPKMAEK

DGCFQSGFNEETCLVKIITGLLEFELVYLEYLQNRFESSEEQARAVQMS

TKVLIQFLQKKAKNLDAITTPDPTTNASLLTKLQAQNQWLQDMTTHLIL

RSFKEFLQSSLRALRQM

Experiments were conducted testing the Fab fragment of the h64-1.4 humanized antibody and demonstrated that it was able to block both cis and trans IL-6 signaling, which is due to site II targeting. The potency of the Fab fragment was unchanged in the presence of soluble IL-6 receptor (sIL-6R). This is in contrast to an anti-IL-6R IgG that had decreased potency in the presence of sIL6R, and that blocks cis signaling only.

These experiments demonstrate that an antibody or fragment of the antibody such as a Fab fragment that targets site II can be used to inhibit both cis and trans signaling of 11-6.

Example 6

Primate Studies

Because non-primate activities can differ greatly from those of primates, candidate IL-6 antagonists are typically further assessed for PK and other parameters using non-human primates. Human IL-6 differs from cynomolgus monkey and rhesus monkey IL-6 at seven sites, one of which is in site II (amino acid 28) and is the same at site II in African green monkey IL-6. This appears to decrease binding of an antibody comprising 018 sequences by only about 3-4 fold. The ability to bind to a non-human primate IL-6 is a useful feature of an IL-6 antagonist, facilitating development of the candidate as a drug, e.g., by enabling testing such as toxicology testing in non-human primates.

As with most IL-6 antibodies, anti-IL-6 antibodies described herein did not cross-react to rodent, rabbit, or canine IL-6 due to low sequence homology. However, in affinity studies, it was found that 018 Fab binds cynomolgus monkey and African green monkey IL-6 with approximately human affinity (Table 2).

TABLE 2

Monovalent affinity (018 Fab) for various IL-6 of various species

| Species | $K_D$ |
|---|---|
| Human | 200 pM |
| African Green Monkey | 280 pM |
| Cynomolgus monkey | 840 Pm |
| Dog | >1 μM |
| Mouse | >1 μM |
| Rabbit | >1 μM |
| Rat | >1 μM |

These data further demonstrate the ability of an IL-6a as described herein to specifically bind and the ability to develop a molecule having features permitting testing, e.g., for toxicology and reproductive studies, in a suitable animal.

Example 7

Increasing Expression of an IL-6a

To increase expression of 018 Fab and 019 Fab polypeptides, constructs were made introducing five additional amino acids (DKTHT (SEQ ID NO: 30)) to the heavy chain in the CH1/hinge region using methods known in the art. The sequence of the altered 018 Fab heavy chain is shown below as SEQ ID NO:24. The altered 018 sequence is referred to herein as 020 and the altered 019 sequence is referred to herein as 021. The 020 molecule (the 020Fab heavy chain and the 018 Fab light chain) had improved expression compared to the parent Fab that had 018Fab heavy and 018 Fab light chains. The 019 molecule exhibited no significant affinity difference compared to the 020 molecule. Expression of both 020 and 019 was increased by about two fold, respectively, and the affinities were not affected by the alteration.

020 Heavy chain (Fab with DKTHT (SEQ ID NO: 30) at the carboxy terminus))

```
                                          (SEQ ID NO: 24)
QVQLVQSGAE VKKPGSSVKV SCKASGYALS NYLIEWVRQA

PGQGLEWMGV ITPGSGTINY AQKFQGRVTI TADESTSTAY

MELSSLRSED TAVYYCARSR WDPLYYYALE YWGQGTTVTV

SSASTKGPSV FPLAPSSKST SGGTAALGCL VKDYFPEPVT

VSWNSGALTS GVHTFPAVLQ SSGLYSLSSV VTVPSSSLGT

QTYICNVNHK PSNTKVDKKV EPKSCDKTHT
```

Figure 3A:
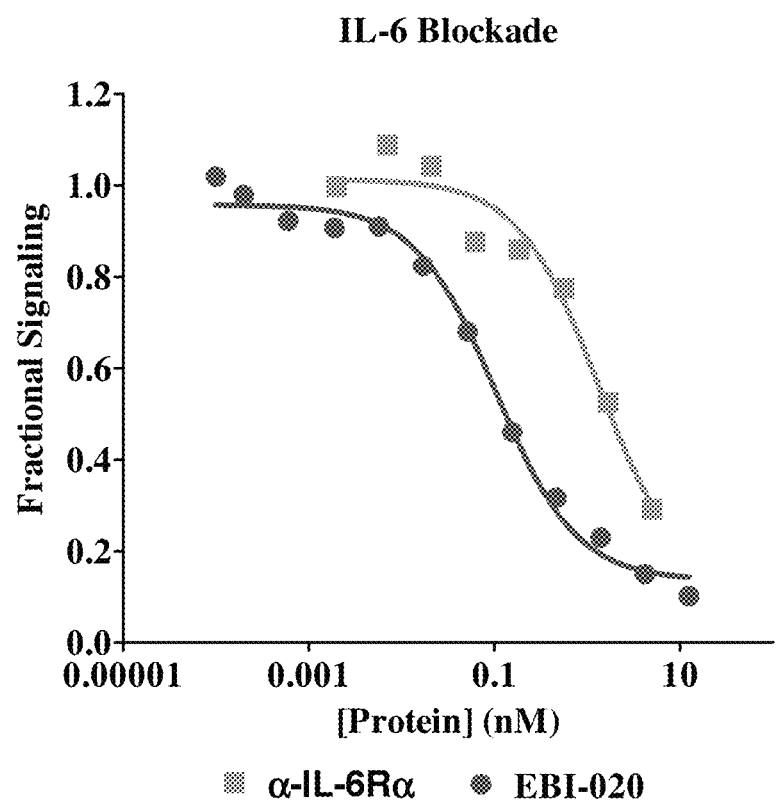
FIG. 3A is a graph illustrating an experiment in which 020 was tested for the ability to block IL-6 signaling in the absence of an excess of soluble IL-6Rα. Experiments were performed in HEK-Blue-IL-6 cells with 0.2 ng/mL IL-6 and 2 μg/mL IL6Rα.
Figure 3B:
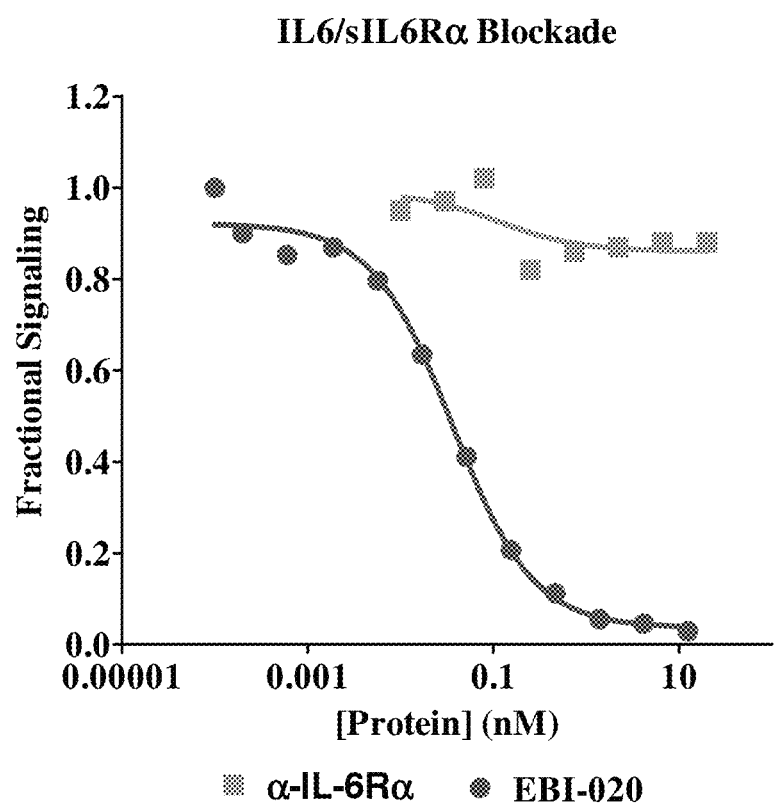
FIG. 3B is a graph illustrating an experiment in which 020 was tested for the ability to block IL-6 signaling in the absence presence of an excess of soluble IL-6Rα. Experiments were performed in HEK-Blue-IL-6 cells with 0.2 ng/mL IL-6 and 2 μg/mL IL6Rα.

IL-6 antagonism using the 020Fab was measured in HEK-Blue™ IL-6 reporter cells (InvivoGen, San Diego, Calif.). Cells were incubated in a mixture of 10 pM IL-6 and varying concentrations of either 020 or IL-6Rα antibody (Cell Sciences, Canton, Mass.), with or without 50 nM IL-6Rα. After 20-24 hours of incubation, 20 μL of cell culture supernatant was mixed with 180 μL of QuantiBlue™ (InvivoGen) substrate and incubated for one hour; the absorbance was then measured at 655 nm. FIG. 3A and FIG. 3B show data from these experiments, demonstrating the ability of 020 to inhibit IL-6 activity in the presence or absence of IL-6R.

Example 8

IgG2 IL-6 Antibodies 018 was reformatted into a human IgG2 isotype framework to reduce FcγR binding and reduce ADCC compared to the IgG1 formatted antibody using methods known in the art. In addition, reformatting 018 to a full-length format, e.g., an IgG2, is expected to decrease the rate of clearance from the vitreous due to the larger size of the molecule.

Construction/Purification of Anti-IL6 IgG2 Antibodies

To construct human IgG2 antibodies using anti-IL-6 sequences described supra, a human IgG2 constant domain was PCR amplified from cDNA with NheI and MluI restriction sites at the N- and C-terminal ends, respectively. The PCR product was purified, digested with NheI and MluI restriction enzymes, and then ligated into pTT5 vector containing anti-IL6 variable domain, i.e., SEQ ID NO:1 (see above). This yielded a full-length IgG2 heavy chain sequence. Plasmids containing the full-length light chain containing the 018 sequence were used to provide light chain.

To further reduce FcRn binding and thereby reduce recycling of the IL-6a, point mutations were made in the heavy chain. The mutations were made by QuikChange® mutagenesis (Agilent Technologies, Santa Clara, Calif.). The heavy and light chain plasmids were co-transfected using poly(ethylenimine) (PEI) into 100 mL transient cultures of HEK293-6E cells and cultured to allow expression for about five days. This generated antibodies containing an anti-IL-6 site II binding moiety and IgG2 structure. Such structures containing 018 CDRs are termed herein 018IgG2 or 029. The point mutations were made at residues I253

The IgG2 molecule was well expressed and blocks IL-6 in cellular assays with slightly improved potency compared to the 020Fab.

029 Mature Sequences (CDRs Underlined)

029 Heavy Chain

```
                                          (SEQ ID NO: 11)
QVQLVQSGAE VKKPGSSVKV SCKASGYALS NYLIEWVRQA

PGQGLEWMGV ITPGSGTINY AQKFQGRVTI TADESTSTAY

MELSSLRSED TAVYYCARSR WDPLYYYALE YWGQGTTVTV

SSASTKGPSV FPLAPCSRST SESTAALGCL VKDYFPEPVT

VSWNSGALTS GVHTFPAVLQ SSGLYSLSSV VTVPSSNFGT

QTYTCNVDHK PSNTKVDKTV ERKCCVECPP CPAPPVAGPS

VFLFPPKPKD TLMISRTPEV TCVVVDVSHE DPEVQFNWYV

DGVEVHNAKT KPREEQFNST FRVVSVLTVV HQDWLNGKEY

KCKVSNKGLP APIEKTISKT KGQPREPQVY TLPPSREEMT

KNQVSLTCLV KGFYPSDIAV EWESNGQPEN NYKTTPPMLD

SDGSFFLYSK LTVDKSRWQQ GNVFSCSVMH EALHNHYTQK

SLSLSPGK
```

029 Light Chain

```
                                          (SEQ ID NO: 12)
DIVMTQSPDS LAVSLGERAT INCRASESVD NYGIPFMNWY

QQKPGQPPKL LIYAASNRGS GVPDRFSGSG SGTDFTLTIS

SLQAEDVAVY YCQQSEEVPL TFGQGTKLEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

Altered FcRn Binding

IL-6 can have certain positive systemic effects. It is therefore an advantage to engineer an IL-6a that has good retention in the vitreous but has a limited systemic half-life. The reduction or elimination of FcRn binding should reduce systemic accumulation of any drug that escapes into circulation, thereby improving safety of an IL-6a.

Accordingly, because FcRn mediated trafficking may increase the efflux of antibodies from the eye, the 020 IgG2 was further modified to ablate FcRn binding by introducing Fc mutations at residues I254, H311, or H436 (See SEQ ID NO:23) numbering according to Martin et al., Molecular Cell, 7:4, 867-877 (2001)). The mutated sites are shown in boldface in SEQ ID NO:23; I254 was mutated to A or R, H311 was mutated to A or E, H311 was mutated to N with D 313 mutated to T, and H436 was mutated to A (numbering starts after the leader sequence, which is underlined in SEQ ID NO:23. IL-6 antagonists containing such sequences are termed 018IgG2m.

Anti-IL-6 Heavy Chain (IgG2) (Regular Font: VH; Italic Font: CH) (without Leader Sequence) Showing Mutation Sites (Boldface)

```
                                        (SEQ ID NO: 23)
QVQLVQSGAE VKKPGSSVKV SCKASGYALS NYLIEWVRQA

PGQGLEWMGV ITPGSGTINY AQKFQGRVTI TADESTSTAY

MELSSLRSED TAVYYCARSR WDPLYYYALE YWGQGTTVTV

SSASTKGPSV FPLAPCSRST SESTAALGCL VKDYFPEPVT

VSWNSGALTS GVHTFPAVLQ SSGLYSLSSV VTVPSSNFGT

QTYTCNVDHK PSNTKVDKTV ERKCCVECPP CPAPPVAGPS

VFLFPPKPKD TLM ISRTPEV TCVVVDVSHE DPEVQFNWYV

DGVEVHNAKT KPREEQFNST FRVVSVLTVV HQDWLNGKEY

KCKVSNKGLP APIEKTISKT KGQPREPQVY TLPPSREEMT

KNQVSLTCLV KGFYPSDIAV EWESNGQPEN NYKTTPPMLD

SDGSFFLYSK LTVDKSRWQQ GNVFSCSVMH EALHNHYTQK

SLSLSPGK
```

Anti-IL-6 Heavy Chain (IgG2) (Regular Font: VH; Italic Font: CH) with Leader Sequence (Underlined) Showing Mutation Sites (Boldface)

```
                                        (SEQ ID NO: 28)
MDWTWRILFLVAAATGAHSQVQLVQSGAE VKKPGSSVKV

SCKASGYALS NYLIEWVRQA PGQGLEWMGV ITPGSGTINY

AQKFQGRVTI TADESTSTAY MELSSLRSED TAVYYCARSR

WDPLYYYALE YWGQGTTVTV SSASTKGPSV FPLAPCSRST

SESTAALGCL VKDYFPEPVT VSWNSGALTS GVHTFPAVLQ

SSGLYSLSSV VTVPSSNFGT QTYTCNVDHK PSNTKVDKTV

ERKCCVECPP CPAPPVAGPS VFLFPPKPKD TLM ISRTPEV

TCVVVDVSHE DPEVQFNWYV DGVEVHNAKT KPREEQFNST

FRVVSVLTVV HQDWLNGKEY KCKVSNKGLP APIEKTISKT

KGQPREPQVY TLPPSREEMT KNQVSLTCLV KGFYPSDIAV

EWESNGQPEN NYKTTPPMLD SDGSFFLYSK LTVDKSRWQQ

GNVFSCSVMH EALHNHYTQK SLSLSPGK
```

Accordingly, some embodiments include an antibody having the heavy chain sequence depicted in SEQ ID NO:23 with mutations at I254 (e.g., A or R), H311 (mutated to A or E), H436 (mutated to A), or D313 (mutated to T) with H311 mutated to N.

SEQ ID NO:25 therefore provides a sequence that, when mutated at I133 (e.g., I133A or I133R), H190 (e.g., H190A or H190E), H315 (e.g., H315A), or D192 with H190 (e.g., D192T with H190N) can be used in an antibody, fragment, or derivative thereof to produce a polypeptide having reduced Fc binding at low pH, e.g., pH 5.5 or lysosomal pH and/or a polypeptide having reduced systemic half-life compared to a parent or other reference molecule that does not include the sequence.

```
                                        (SEQ ID NO: 25)
SASTKGPSV  FPLAPCSRST SESTAALGCL VKDYFPEPVT

VSWNSGALTS GVHTFPAVLQ SSGLYSLSSV VTVPSSNFGT

QTYTCNVDHK PSNTKVDKTV ERKCCVECPP CPAPPVAGPS

VFLFPPKPKD TLMISRTPEV TCVVVDVSHE DPEVQFNWYV

DGVEVHNAKT KPREEQFNST FRVVSVLTVV HQDWLNGKEY

KCKVSNKGLP APIEKTISKT KGQPREPQVY TLPPSREEMT

KNQVSLTCLV KGFYPSDIAV EWESNGQPEN NYKTTPPMLD

SDGSFFLYSK LTVDKSRWQQ GNVFSCSVMH EALHNHYTQK

SLSLSPGK
```

Anti-IL-6 Light Chain (IgG2) (Regular Font: VK; Italic Font: CK)

```
                                        (SEQ ID NO: 22)
DIVMTQSPDSLAVSLGERATINCRASESVDNYGIPFMNWYQQK

PGQPPKLLIYAASNRGSGVPDRFSGSGSGTDFTLTISSLQAED

VAVYYCQQSEEVPLTFGQGTKLEIKRTVAAPSVF IFPPSDEQLK

SGTASVVCLL NNFYPREAKV QWKVDNALQS GNSQESVTEQ

DSKDSTYSLS STLTLSKADY EKHKVYACEV THQGLSSPVT

KSFNRGEC
```

Example 9

Formulation Stability

The stability of the anti-IL-6/IgG1 Fab fragment (containing the IgG1CH1 domain) was tested by determining the $T_m$ initially in PBS then in a range of buffers and excipients using differential scanning fluorimetry. It was found that citrate buffer, pH 5.5 increased the $T_m$ to more than 80° C. Accordingly, in some embodiments, an IL-6a is provided in citrate buffer and in some cases has a $T_m$ of at least 80° C.

Aggregation was tested using SEC-MALS and no aggregation was observed at 20 mg/ml in phosphate buffered saline (PBS).

Example 10 pH Sensitive Antibodies for Enhanced PK

IL-6 can have certain positive systemic effects. It is therefore an advantage to engineer an IL-6a that has good retention in the vitreous but has a limited systemic half-life. The reduction or elimination of FcRn binding should reduce systemic accumulation of any drug that escapes into circulation, thereby improving safety of an IL-6a. Accordingly, because FcRn mediated trafficking may increase the efflux of antibodies from the eye, the 020 IgG2 was further modified to ablate FcRn binding by introducing Fc mutations at residues I253, H310, or H435 (numbering according to Martin et al. (Molecular Cell, 7:4, 867-877 (2001))). Such antibodies are referred to herein as IL-6 pH antibodies or anti-IL-6 pH and are further described below.

Generation of IL-6ipH Antibodies

The pKa of histidine is about 6.0 and histidines inserted at binding interfaces can disrupt binding upon side-chain protonation at low pH. Using an anti-IL-6 site II targeted antibody as described herein, a library was generated containing histidine-rich variants of CDRs from 018 and the library was screened for pH-sensitive binding using yeast display. The library generated was a combinatorial library with CDRs encoded by degenerate codons such that each residue is either a wild-type residue (i.e., the same as in the parental antibody) or a histidine residue. The screening was performed by alternating sorting for high binding at physiological pH (7.4) and low binding at endosomal pH (5.5).

A yeast-selected mutant was identified that had relatively high binding at pH 7.4 (monovalent Kd of 407 pM for the mutant compared to 192 pM for the parent molecule) and relatively low binding at pH 5.5 (monovalent Kd of 2.362 nM for the mutant compared to 195 pM for the parent). This constitutes an approximately 5.8 fold change in the affinity at pH 5.5. This mutant contained multiple histidine mutations in the light chain CDR1. Thus, the mutant demonstrated similar binding to the parent molecule at pH 7.4, and a significant loss of affinity at pH 5.5. This observation was verified using ELISA, FACS, and SPR analysis by methods known in the art.

These data demonstrate that an IL-6a that is based on an antibody can be created that has the features of an anti-IL-6 targeting site II of IL-6 that can be used to inhibit both cis and trans activity of IL-6, and have increased PK compared to a parent antibody or other antibody having a wild type Fc domain effected at least in part by altered binding at pH 5.5.

Example 11

Efficacy of Local IL-6 Blockade in Mouse Laser Choroidal Neovascularization (CNV) Model To determine whether local IL-6 blockade could be effective for treating eye disease, e.g., diabetic macular edema (DME) or wet AMD, a monoclonal anti-IL-6 antibody was locally administered in a model system for choroidal neovascularization. The laser-induced CNV model as described in Saishin et al. Journal of Cellular Physiology, 195:241-248 (2003) was employed in this Example. A laser-induced CNV model reproduces many of the pathologic processes underlying diabetic macular edema (DME), including inflammation and angiogenesis.

A monoclonal anti-mouse IL-6 antibody (MP5-20F3, which is a rat IgG1 isotype antibody purchased from Bio X Cell, catalog number BE0046) was administered to the test group by intravitreal (IVT) injection. Controls received intravitreal injection of VEGF trap or intravitreal injection of an anti-HRP isotype control antibody (a rat IgG1 against horseradish peroxidase, clone HRPN, purchased from BioXCell; catalog number BE0088). For all antibody groups, 20 µg of protein in a 1 µL volume was injected into the test eye, while the contralateral eye was left untreated as a further control.

Figure 4:
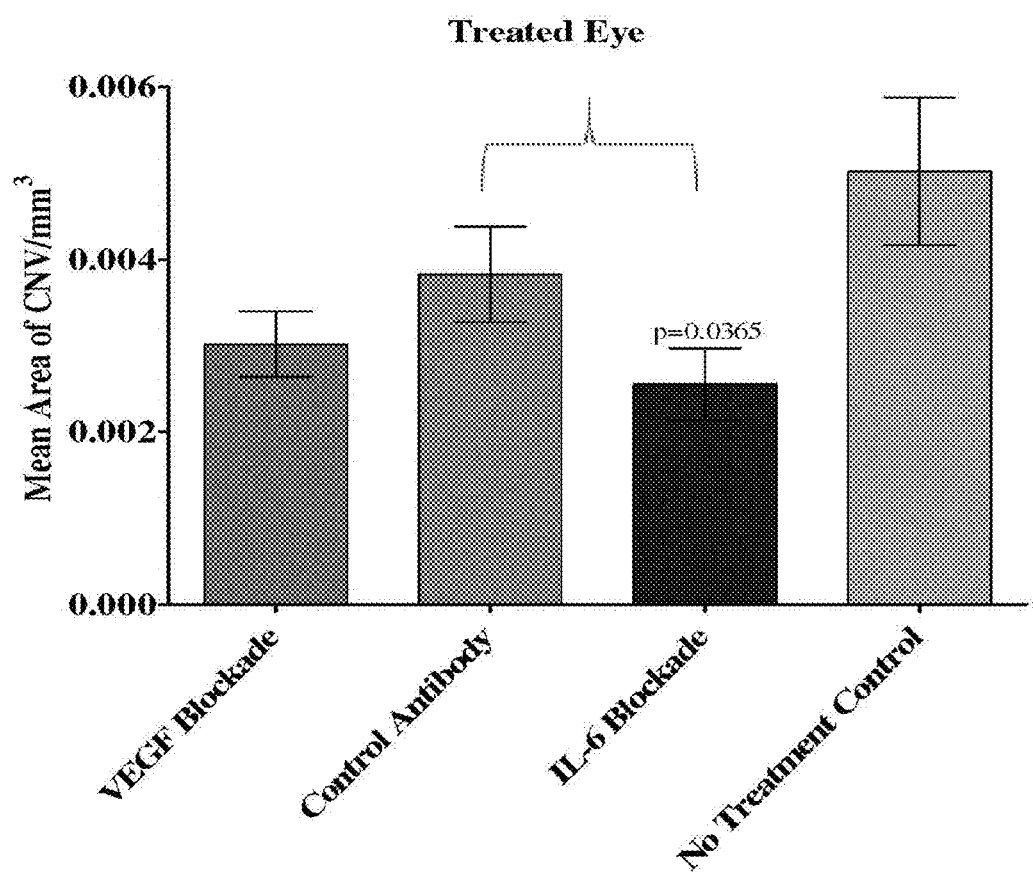
FIG. 4 is a graph illustrating the results of an experiment in which a monoclonal anti-IL-6 antibody ("IL-6 Blockade") was administered IVT in a mouse CNV model. Controls were no treatment (contralateral eye), intravitreal injection of an anti-VEGF antibody ("VEGF Blockade") or intravitreal injection of an anti-HRP isotype control antibody ("Control Antibody").

Mice were euthanized on day 7 after laser and choroidal flat mounts were stained with Griffonia Simplicifolia (GSA) lectin to measure the lesion area. FIG. 4 shows the results. The anti-IL-6 antibody treated group showed a statistically significant reduction in neovascularization compared to the control antibody treated group ($p<0.05$). On average the anti-IL-6 antibody treated group also showed reduced neovascularization compared with the anti-VEGF positive control.

These data demonstrate that an IL-6a, e.g., a monoclonal anti-IL-6 antibody, administered IVT can significantly reduce neovascularization in a mouse CNV model. The results further suggest that an anti-IL-6 antibody can produce a reduction in neovascularization at least as great, and possibly greater, than an anti-VEGF antibody. These data indicate that local inhibition of IL-6 is useful for treating eye diseases such as diseases involving vascular leakage, e.g., wet AMD or macular edema, e.g., diabetic macular edema.

Other embodiments are within the scope of the following claims.

---

What is claimed is:

1. An isolated antibody or antigen binding fragment thereof comprising
   a) a light chain variable (VL) domain comprising an amino sequence that is at least 95% identical to a VL domain as set forth in amino acids 1-111 of SEQ ID NO: 22, and
   b) a heavy chain variable (VH) domain comprising an amino sequence that is at least 95% identical to a VH domain as set forth in amino acids 1-121 of SEQ ID NO: 23.

2. The isolated antibody or antigen binding fragment of claim 1, wherein the antibody or fragment thereof comprises:
   a) CDR sequences that in combination differ by no more than 5 amino acids from a VH CDR1 as set forth in SEQ ID NO:4, a VH CDR2 as set forth in SEQ ID NO:5, and VH CDR3 as set forth in SEQ ID NO:6; and
   b) CDR sequences that in combination differ by no more than 5 amino acids from a VL CDR1 as set forth in SEQ ID NO:7, a VL CDR2 as set forth in SEQ ID NO:8, and a VL CDR3 as set forth in SEQ ID NO:9.

3. The isolated antibody or antigen binding fragment of claim 1, comprising
   a) a VH CDR1 as set forth in SEQ ID NO:4, a VH CDR2 as set forth in SEQ ID NO:5, and VH CDR3 as set forth in SEQ ID NO:6; and
   b) a VL CDR1 as set forth in SEQ ID NO:7, a VL CDR2 as set forth in SEQ ID NO:8, and a VL CDR3 as set forth in SEQ ID NO:9.

4. The isolated antibody or antigen binding fragment of claim 1, wherein the antibody or fragment thereof comprises:
   a) CDR sequences that in combination differ by no more than 4 amino acids from a VH CDR1 as set forth in SEQ ID NO:4, a VH CDR2 as set forth in SEQ ID NO:5, and VH CDR3 as set forth in SEQ ID NO:6; and
   b) CDR sequences that in combination differ by no more than 4 amino acids from a VL CDR1 as set forth in SEQ ID NO:7, a VL CDR2 as set forth in SEQ ID NO:8, and a VL CDR3 as set forth in SEQ ID NO:9.

5. The isolated antibody or antigen binding fragment of claim 1, wherein the antibody or fragment thereof comprises:
   a) CDR sequences that in combination differ by no more than 3 amino acids from a VH CDR1 as set forth in SEQ ID NO:4, a VH CDR2 as set forth in SEQ ID NO:5, and VH CDR3 as set forth in SEQ ID NO:6; and
   b) CDR sequences that in combination differ by no more than 3 amino acids from a VL CDR1 as set forth in SEQ ID NO:7, a VL CDR2 as set forth in SEQ ID NO:8, and a VL CDR3 as set forth in SEQ ID NO:9.

6. The isolated antibody or antigen binding fragment of claim 1, wherein the antibody or fragment thereof comprises:
   a) CDR sequences that in combination differ by no more than 2 amino acids from a VH CDR1 as set forth in SEQ ID NO:4, a VH CDR2 as set forth in SEQ ID NO:5, and VH CDR3 as set forth in SEQ ID NO:6; and
   b) CDR sequences that in combination differ by no more than 2 amino acids from a VL CDR1 as set forth in SEQ ID NO:7, a VL CDR2 as set forth in SEQ ID NO:8, and a VL CDR3 as set forth in SEQ ID NO:9.

7. The isolated antibody or antigen binding fragment of claim 1, wherein the antibody or fragment thereof comprises:
   a) CDR sequences that in combination differ by no more than 1 amino acid from a VH CDR1 as set forth in SEQ ID NO:4, a VH CDR2 as set forth in SEQ ID NO:5, and VH CDR3 as set forth in SEQ ID NO:6; and
   b) CDR sequences that in combination differ by no more than 1 amino acid from a VL CDR1 as set forth in SEQ ID NO:7, a VL CDR2 as set forth in SEQ ID NO:8, and a VL CDR3 as set forth in SEQ ID NO:9.

8. The isolated antibody or antigen binding fragment of claim 1, wherein the antibody is an IgG2 antibody.

9. A composition comprising the antibody or antigen binding fragment of claim 1.

10. A composition comprising the antibody or antigen binding fragment of claim 2.

11. A method of treating a subject having an ocular disease characterized by an elevated level of interleukin-6 (IL-6) in the vitreous, the method comprising administering to the subject the antibody or antigen binding fragment of claim 3.

12. The method of claim 11, wherein the ocular disease is selected from the group consisting of diabetic macular edema (DME), diabetic retinopathy, uveitis, dry eye syndrome, uveitis, age-related macular degeneration (AMD), proliferative diabetic retinopathy (PDR), retinal vein occlusion (RVO), neuromyelitis optica (NMO), corneal transplant, corneal abrasion, and physical injury to the eye.

13. The method of claim 12, wherein the ocular disease is DME.

14. The method of claim 11, wherein the antibody or antigen binding fragment is delivered to the vitreous of the subject's eye.

15. The method of claim 11, wherein the ocular disease is diabetic macular edema and the antibody or antigen binding fragment thereof is delivered to the vitreous of the subject's eye.

16. An isolated antibody or antigen binding fragment, comprising
   a) a VH CDR1 as set forth in SEQ ID NO: 4, a VH CDR2 as set forth in SEQ ID NO:5, and VH CDR3 as set forth in SEQ ID NO:6; and
   b) a VL CDR1 as set forth in SEQ ID NO:7, a VL CDR2 as set forth in SEQ ID NO:8, and a VL CDR3 as set forth in SEQ ID NO:9.

17. A method of treating a subject having an ocular disease characterized by an elevated level of interleukin-6 (IL-6) in the vitreous, the method comprising administering to the subject the antibody or antigen binding fragment of claim 16.

18. The method of claim 17, wherein the ocular disease is selected from the group consisting of diabetic macular edema (DME), diabetic retinopathy, uveitis, dry eye syndrome, uveitis, age-related macular degeneration (AMD), proliferative diabetic retinopathy (PDR), retinal vein occlusion (RVO), neuromyelitis optica (NMO), corneal transplant, corneal abrasion, and physical injury to the eye.

19. The method of claim 18, wherein the ocular disease is DME.

20. The method of claim 17, wherein the ocular disease is diabetic macular edema and the antibody or antigen binding fragment thereof is delivered to the vitreous of the subject's eye.

\* \* \* \* \*